(12) United States Patent
Maeda

(10) Patent No.: US 11,471,123 B2
(45) Date of Patent: Oct. 18, 2022

(54) ULTRASOUND DIAGNOSTIC APPARATUS, PROGRAM, AND METHOD OF OPERATING ULTRASOUND DIAGNOSIS APPARATUS

(71) Applicant: Hitachi, Ltd., Tokyo (JP)

(72) Inventor: Toshinori Maeda, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 585 days.

(21) Appl. No.: 16/361,446

(22) Filed: Mar. 22, 2019

(65) Prior Publication Data

US 2020/0046316 A1 Feb. 13, 2020

(30) Foreign Application Priority Data

Aug. 9, 2018 (JP) .............................. JP2018-149937

(51) Int. Cl.
 *A61B 8/00* (2006.01)
 *A61B 8/08* (2006.01)
 (Continued)

(52) U.S. Cl.
 CPC .......... *A61B 8/0866* (2013.01); *A61B 8/0883* (2013.01); *A61B 8/461* (2013.01);
 (Continued)

(58) Field of Classification Search
 CPC ..... A61B 8/0866; A61B 8/0883; A61B 8/461; A61B 8/5207; A61B 8/02; A61B 8/4444;
 (Continued)

(56) References Cited

U.S. PATENT DOCUMENTS

| 5,090,411 A | 2/1992 | Higuchi |
| 2008/0269611 A1 | 10/2008 | Pedrizzetti et al. |

(Continued)

FOREIGN PATENT DOCUMENTS

| CN | 101297762 A | 11/2008 |
| CN | 101658432 A | 3/2010 |

(Continued)

OTHER PUBLICATIONS

Chinese-language Office Action issued in Chinese Application No. 201910224255.9 dated Nov. 18, 2021 with English translation (20 pages).

(Continued)

*Primary Examiner* — Joel Lamprecht
(74) *Attorney, Agent, or Firm* — Crowell & Moring LLP

(57) ABSTRACT

A temporal change at each coordinate of interest which is spatially fixed in frame data of a plurality of time phases obtained by transmitting and receiving ultrasound is made understandable. A trace processor derives an amount of temporal change at each coordinate of interest of a plurality of coordinates of interest which are spatially fixed in the frame data over a plurality of time phases. The trace processor also derives an amount of spatial movement of each site of interest based on the amount of temporal change of each coordinate of interest near each site of interest. Further, the trace processor derives an amount of spatial movement of each site of interest for each time phase over a plurality of time phases in a trace period, and traces a motion of each site of interest in the trace period based on the amount of movement derived for each time phase.

10 Claims, 18 Drawing Sheets

(51) Int. Cl.
    *G06T 7/215*    (2017.01)
    *A61B 8/02*    (2006.01)
(52) U.S. Cl.
    CPC ............... *A61B 8/5207* (2013.01); *A61B 8/02*
        (2013.01); *A61B 8/4444* (2013.01); *A61B*
        *8/469* (2013.01); *G06T 7/215* (2017.01); *G06T*
            *2207/10132* (2013.01); *G06T 2207/30048*
                                    (2013.01)
(58) Field of Classification Search
    CPC ......... A61B 8/469; A61B 8/42; A61B 8/5223;
            G06T 7/215; G06T 2207/10132; G06T
                            2207/30048; G06T 7/246
    See application file for complete search history.

(56) References Cited

U.S. PATENT DOCUMENTS

| | | | |
|---|---|---|---|
| 2010/0056918 A1 | 3/2010 | Sato et al. | |
| 2010/0056919 A1* | 3/2010 | Abe | A61B 8/08 600/443 |
| 2010/0094133 A1 | 4/2010 | Yoshiara et al. | |
| 2010/0286525 A1 | 11/2010 | Osumi | |
| 2012/0008833 A1 | 1/2012 | Song et al. | |
| 2012/0121149 A1 | 5/2012 | Murashita | |
| 2013/0072794 A1 | 3/2013 | Waki | |
| 2013/0158399 A1 | 6/2013 | Chono et al. | |
| 2015/0094584 A1 | 4/2015 | Abe et al. | |
| 2015/0250446 A1 | 9/2015 | Kanayama | |
| 2015/0257731 A1 | 9/2015 | Abe | |
| 2017/0251998 A1 | 9/2017 | Maeda et al. | |
| 2018/0055487 A1 | 3/2018 | Abe et al. | |

FOREIGN PATENT DOCUMENTS

| | | | |
|---|---|---|---|
| CN | 101721226 A | 6/2010 | |
| CN | 101879073 A | 11/2010 | |
| CN | 102939050 A | 2/2013 | |
| CN | 104080408 A | 10/2014 | |
| CN | 104114102 A | 10/2014 | |
| CN | 106604683 A | 4/2017 | |
| JP | 2006-55266 A | 3/2006 | |
| JP | 2007-130063 A | 5/2007 | |
| JP | 2012-105750 A | 6/2012 | |
| JP | 2015-91299 A | 5/2015 | |
| JP | 2016-55040 A | 4/2016 | |
| JP | 5918325 B2 | 5/2016 | |
| JP | 5999935 B2 | 9/2016 | |
| WO | WO 2012/029616 A1 | 3/2012 | |

OTHER PUBLICATIONS

Japanese-language Office Action issued in Japanese Application No. 2018-149937 dated Jan. 18, 2022 with English translation (eight (8) pages).

* cited by examiner

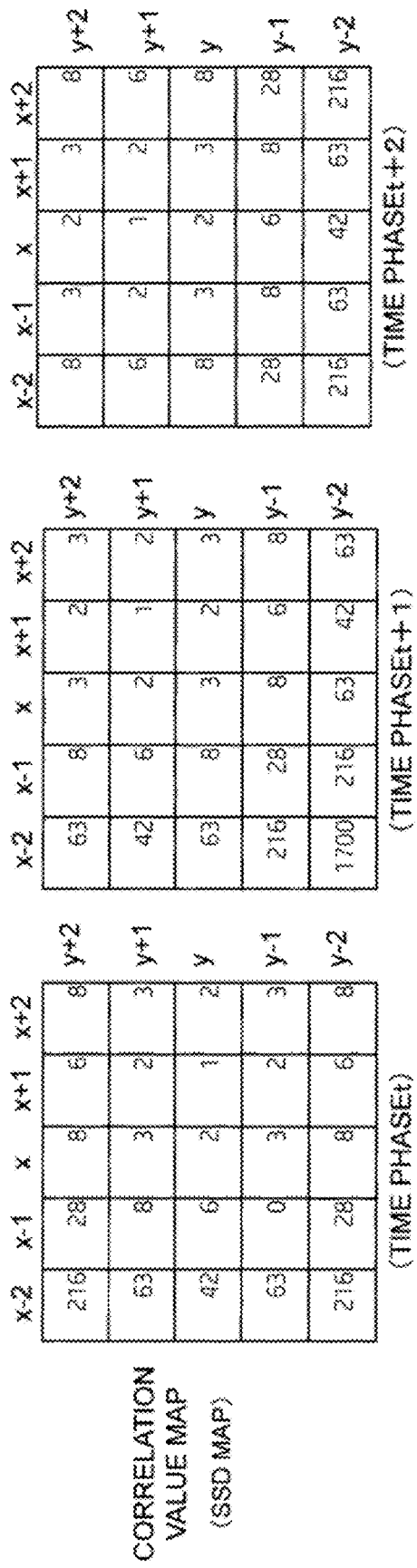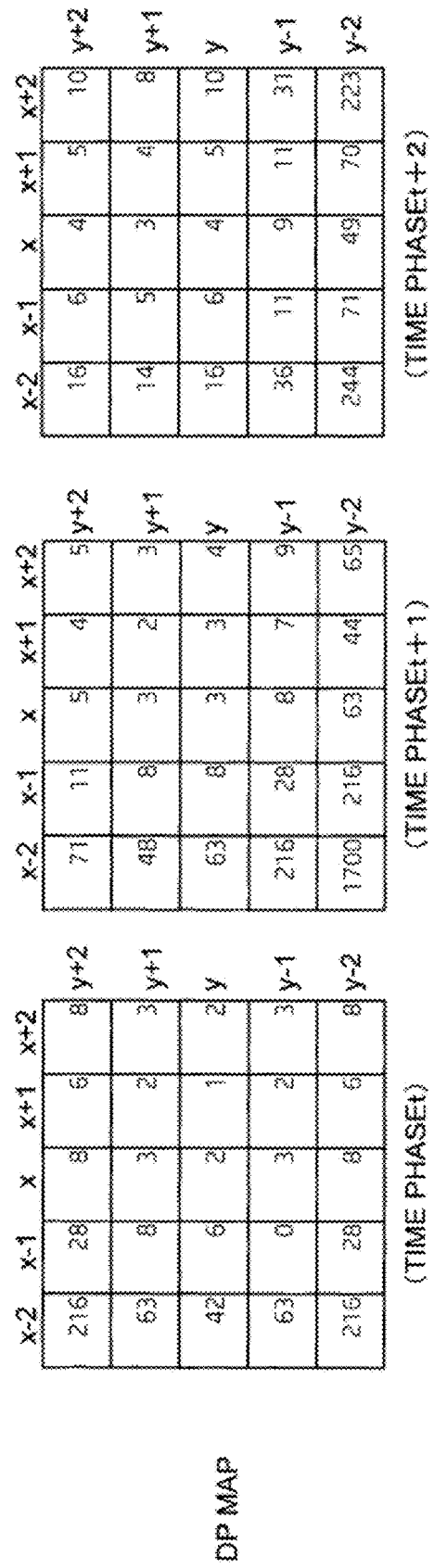
FIG. 14

ULTRASOUND DIAGNOSTIC APPARATUS, PROGRAM, AND METHOD OF OPERATING ULTRASOUND DIAGNOSIS APPARATUS

CROSS REFERENCE TO RELATED APPLICATION

This application claims priority to Japanese Patent Application No. 2018-149937 filed on Aug. 9, 2018, which is incorporated herein by reference in its entirety including the specification, claims, drawings, and abstract.

TECHNICAL FIELD

The present disclosure relates to an ultrasound diagnostic apparatus, a program, and a method of operating an ultrasound diagnostic apparatus.

BACKGROUND

Ultrasound diagnostic apparatuses are used for diagnosing a tissue or the like in a living body, and play an important role in, for example, diagnosis of a fetus or the like.

For example, JP 5918325 B discloses an ultrasound diagnostic apparatus which traces a motion of a measurement point related to a heart of a fetus. JP 5918325 B discloses a process in which a tracing process is executed for each of a plurality of trace points including the measurement point and auxiliary points of the measurement point, and which traces the motion of the measurement point by a dynamic programming method which uses a plurality of trace results obtained from the plurality of trace points.

There is also known, for example, an ultrasound diagnostic apparatus which is used for diagnosis of plaques adhered to a vascular wall, as disclosed in JP 599935 B, and an ultrasound diagnostic apparatus which displays a motion of a cardiac muscle related to a direction of a myofibrosis cordis, as disclosed in JP 2015-91299 A.

It is known that, in an ultrasound image based on data obtained by transmitting and receiving ultrasound, a speckle pattern is generated. The speckle pattern may sometimes adversely affect the tracing process of a site of interest in the ultrasound image. For example, when the motion of the site of interest in the ultrasound image is to be traced by a pattern matching process of the image or the like, there is a possibility that a position of another site corresponding to a speckle pattern which is accidentally similar to the speckle pattern of the site of interest is erroneously recognized as a destination of the movement of the site of interest.

In consideration of this, in JP 5918325 B, in tracing the motion of the measurement point, the tracing process is executed for each trace point, for the plurality of trace points including the measurement points and the auxiliary points thereof. With an epoch-making process of tracing the motion of the measurement points using the plurality of trace results obtained from the plurality of trace points, the adverse influence of the speckle pattern is reduced or avoided, to thereby improve precision of the tracing of the measurement points.

In the process described in JP 5918325 B, in obtaining the trace result of each trace point, an evaluation value map related to a spatial motion of each trace point is used. In other words, the process of JP 5918325 B focuses on the spatial motion (spatial change) of each of the moving trace points.

In the contrary, in the present disclosure, the principle of the tracing process is reconsidered from the root, and the present disclosure focuses on a temporal changes at positions which are spatially fixed. The temporal changes at spatially fixed positions can also be expected for application to various processes other than the tracing process.

An advantage of the present disclosure lies in enabling understanding of a temporal change at each coordinate of interest which is spatially fixed in frame data of a plurality of time phases obtained by transmitting and receiving ultrasound.

SUMMARY

According to one aspect of the present disclosure, there is provided an ultrasound diagnostic apparatus, configured to: set frame data of a plurality of time phases obtained by transmitting and receiving ultrasound as a processing target; and derive an amount of temporal change at each coordinate of interest of a plurality of coordinates of interest which are spatially fixed in the frame data over the plurality of time phases.

According to the present disclosure, a temporal change at each coordinate of interest which is spatially fixed in the frame data of a plurality of time phases obtained by transmitting and receiving ultrasound can be understood. For example, an amount of spatial movement of one or more sites of interest may be derived based on an amount of temporal change at one or more coordinates of interest, so as to improve the precision of the amount of spatial motion. Alternatively, for example, with the use of the dynamic programming in a direction of a time axis in deriving the amount of temporal change at each coordinate of interest, the amount of temporal change at each coordinate of interest may be optimized. Alternatively, for example, with the use of a parabola fitting in a spatial direction in deriving the amount of temporal change at each coordinate of interest, the precision of the amount of temporal change at each coordinate of interest may be improved.

BRIEF DESCRIPTION OF DRAWINGS

Embodiment(s) of the present disclosure will be described by reference to the following figures, wherein:

FIG. 14 is a diagram showing a specific example of a DP map;

DESCRIPTION OF EMBODIMENTS

Figure 1:
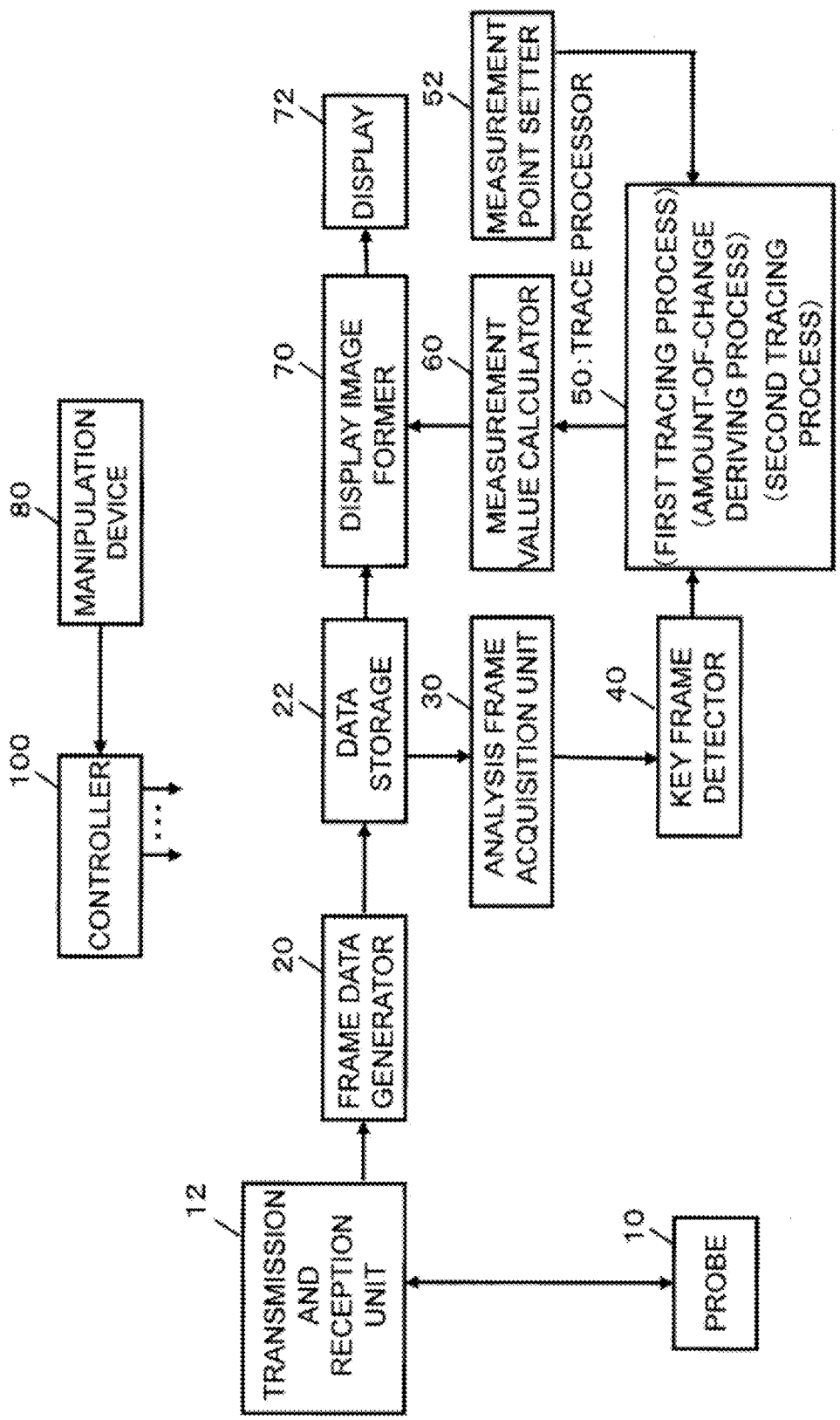
FIG. 1 is a diagram showing a specific example structure of an ultrasound diagnostic apparatus according to an embodiment of the present disclosure.

An overview of an embodiment of the present disclosure will first be described. An ultrasound diagnostic apparatus according to the present embodiment sets frame data of a plurality of time phases obtained by transmitting and receiving ultrasound as a processing target, and derives an amount of temporal change at each coordinate of interest of a plurality of coordinates of interest which are spatially fixed in the frame data over the plurality of time phases.

Because each coordinate of interest is spatially fixed, for example, when there is a spatial motion (which includes at least one of a transfer or a movement) in a tissue which is a diagnosis target, the tissue would relatively move with respect to each coordinate of interest which is spatially fixed, and a tissue portion corresponding to each coordinate of interest changes in time.

In consideration of this, the ultrasound diagnostic apparatus according to the present embodiment may derive, for example, an amount of temporal change of the tissue at a fixed position corresponding to each coordinate of interest, as the amount of temporal change at each coordinate of interest. For example, there may be derived an amount of change which indicates in which direction and how fast the tissue portion corresponding to each coordinate of interest is to move.

The amount of temporal change at each coordinate of interest may be a scalar quantity such as a numerical value, or a vector quantity having a magnitude and a direction. For example, for frame data corresponding to a two-dimensional region, a two-dimensional vector quantity may be derived as the amount of temporal change at each coordinate of interest. For frame data corresponding to a three-dimensional region (when a plurality of frame data form a three-dimensional region), a three-dimensional vector quantity may be derived as the amount of temporal change at each coordinate of interest.

Further, in deriving the amount of temporal change at each coordinate of interest, the ultrasound diagnostic apparatus of the present embodiment may derive an optimized amount of change at each coordinate of interest by applying dynamic programming in a direction of a time axis. Here, "optimize" refers to a process of causing a change having correlation in the time axis direction (that is, there is no sudden change to a completely different direction between consecutive time phases), and "derive an optimized amount of change" refers to a process of deriving an amount of change, with a change having a correlation in the time axis direction (that is, deriving an amount of change which does not suddenly change in a completely different direction between consecutive time phases). In addition, the ultrasound diagnosis apparatus according to the present embodiment may derive the amount of change at each coordinate of interest in units (for example, a fraction) smaller than a unit of pixel (for example, an integer), by applying parabola fitting in the spatial direction.

Further, the ultrasound diagnostic apparatus of the present embodiment may execute various processes using the amount of temporal change at each coordinate of interest of the plurality of coordinates of interest. For example, a display image showing the amount of temporal change at each coordinate of interest of the plurality of coordinates of interest may be formed and displayed. Alternatively, for example, information showing properties of the diagnosis target tissue may be generated from the amount of temporal change at each coordinate of interest of the plurality of coordinates of interest.

Moreover, using the amount of temporal change at each coordinate of interest of the plurality of coordinates of interest, the ultrasound diagnostic apparatus of the present embodiment may, for example, derive an amount of spatial movement of a site of interest or execute a tracing process of a site of interest which moves spatially. Further, a display image showing the amount of spatial movement of the site of interest may be formed and displayed.

The overview of the ultrasound diagnostic apparatus according to the present embodiment has been described. Next, a specific example of the ultrasound diagnostic apparatus according to the present embodiment will be described with reference to the drawings.

FIG. 1 is a diagram showing a specific example of the ultrasound diagnostic apparatus of the present embodiment. An ultrasound diagnostic apparatus exemplified in FIG. 1 has constituting elements shown with reference numerals.

A probe 10 is an ultrasound probe which transmits and receives ultrasound to and from a diagnosis region including a diagnosis target. The probe 10 has a plurality of transducer elements which transmit and receive ultrasound, and transmission of the plurality of transducer elements is controlled by a transmission and reception unit 12, to form a transmission beam. In addition, the plurality of transducer elements receive ultrasound from the diagnosis region, a signal obtained by the reception is output to the transmission and reception unit 12, and the transmission and reception unit 12 forms a reception beam, to obtain a reception signal (echo data). For the transmission and reception of the ultrasound, techniques such as transmission aperture synthesis or the like may be used. In addition, the probe 10 may be a three-dimensional ultrasound probe which three-dimensionally transmits and receives the ultrasound in a three-dimensional diagnosis region, or a two-dimensional ultrasound probe which two-dimensionally transmits and receives the ultrasound in a two-dimensional diagnosis region.

The transmission and reception unit 12 has a function as a transmission beam former which outputs a transmission signal to the plurality of transducer elements of the probe 10 and controls the plurality of transducer elements to form a transmission beam. In addition, the transmission and reception unit 12 has a function as a reception beam former which forms the reception signal based on the signals obtained from the plurality of transducer elements of the probe 10 and obtains the reception signal (echo data). The transmission and reception unit 12 may be realized, for example, using an electric or electronic circuit (transmission and reception circuit). In addition, in the realization thereof, hardware such as an ASIC and an FPGA may be used as necessary.

A frame data generator 20 generates frame data of an ultrasound image based on the reception signal (echo data) obtained from the transmission and reception unit 12. The frame data generator 20 applies signal processing such as gain correction, a log compression, a wave detection, an outline emphasis, a filtering process, or the like as necessary on the reception signal, to form, for example, for each time phase, frame data of a tomographic image (B-mode image) including the diagnosis target over a plurality of time phases. In the case where the ultrasound is transmitted and received three-dimensionally, and the reception signal is collected from the three-dimensional diagnosis region, a plurality of frame data which spatially form the three-dimensional diagnosis region may be generated.

A data storage 22 stores frame data generated by the frame data generator 20. The data storage 22 may be realized, for example, using a storage device such as a semiconductor memory, a hard disk drive, or the like.

An analysis frame acquisition unit 30 acquires a plurality of frame data to be an analysis target from among a plurality of frame data stored in the data storage 22. A key frame detector 40 detects a plurality of key frames corresponding to a distinctive time phase from among the plurality of frame data which are the analysis target. A measurement point setter 52 sets one or more sites of interest in the frame data of a particular time phase of the plurality of time phases.

A trace processor 50 executes a tracing process targeted to one or more sites of interest in the tissue which is the diagnosis target. The trace processor 50 executes, for example, a first tracing process (key frame trace) to trace a site of interest, with the plurality of key frames as a processing target.

In addition, the trace processor 50 derives an amount of temporal change at each coordinate of interest of a plurality of coordinates of interest which are spatially fixed in the frame data over a plurality of time phases. For example, the trace processor 50 may sequentially set frame data of a plurality of time phases from one time phase of two key frames to the other time phase, and may derive the amount of temporal change of the tissue at a fixed position corresponding to each coordinate of interest.

Moreover, the trace processor 50 may derive the amount of spatial movement of each site of interest based on, for example, the amount of temporal change of each coordinate of interest near each site of interest. Further, the trace processor 50 may execute a second tracing process to derive an amount of spatial movement of each site of interest for each time phase over a plurality of time phases in a trace period, and to trace the motion of each site of interest in the trace period based on the amount of movement derived for each time phase.

A measurement value calculator 60 calculates a measurement value related to the tissue which is the diagnosis target, based on a trace result of each site of interest in the diagnosis target tissue. A display image former 70 forms a display image to be displayed on a display 72. The display image former 70 forms, for example, a display image showing the measurement value calculated by the measurement value calculator 60. Alternatively, the display image former 70 may form, for example, a display image showing an ultrasound image corresponding to the frame data obtained from the data storage 22.

Each of the frame data generator 20, the analysis frame acquisition unit 30, the key frame detector 40, the trace processor 50, the measurement point setter 52, the measurement value calculator 60, and the display image former 70 may be realized by cooperation of, for example, hardware such as a processor or the like and software (a program) which defines an operation of the processor or the like. In realization of these elements, hardware such as the ASIC and the FPGA may be used as necessary.

The display 72 displays the display image formed by the display image former 70. The display 72 may be realized using, for example, a display device such as a liquid crystal display, an organic EL (electroluminescence) display, or the like.

A controller 100 comprehensively controls the ultrasound diagnostic apparatus of FIG. 1. In the control by the controller 100, a command received from a user through a manipulation device 80 is also reflected. The controller 100 may be realized, for example, by cooperation of hardware such as a CPU, a processor, a memory, or the like, and software (a program) which defines an operation of the CPU, the processor, or the like. The manipulation device 80 is realized, for example, by at least one of a mouse, a keyboard, a trackball, a touch panel, other switches, or the like.

The ultrasound diagnostic apparatus of the specific example shown in FIG. 1 may be realized using, for example, one or more computers. The computer has hardware resources such as a computation device such as the CPU, a storage device such as the memory and the hard disk drive, a communication device which uses a communication line such as the Internet, a device which reads and writes data from and to a storage medium such as an optical disk, a semiconductor memory, a card memory, or the like, a display device such as a display, a manipulation device for receiving manipulation from the user, or the like.

For example, a program (software) corresponding to at least a part of functions of a plurality of portions with reference numerals of the ultrasound diagnostic apparatus exemplified in FIG. 1 is read into the computer and stored in the memory or the like, and at least a part of the functions of the ultrasound diagnostic apparatus exemplified in FIG. 1 is realized by the computer by cooperation of the hardware resources of the computer and the read software. The program may be provided to the computer (ultrasound diagnostic apparatus), for example, via a communication line such as the Internet, or may be stored in a recording medium such as the optical disk, the semiconductor memory, the card memory, or the like and provided to the computer (ultrasound diagnostic apparatus).

The overall structure of the ultrasound diagnostic apparatus exemplified in FIG. 1 has been described. Next, a specific example of processes realized by the ultrasound diagnostic apparatus exemplified in FIG. 1 will be described. The structures shown in FIG. 1 (portions with reference numerals) will be referred to in the following description with the reference numerals used in FIG. 1.

Figure 2:
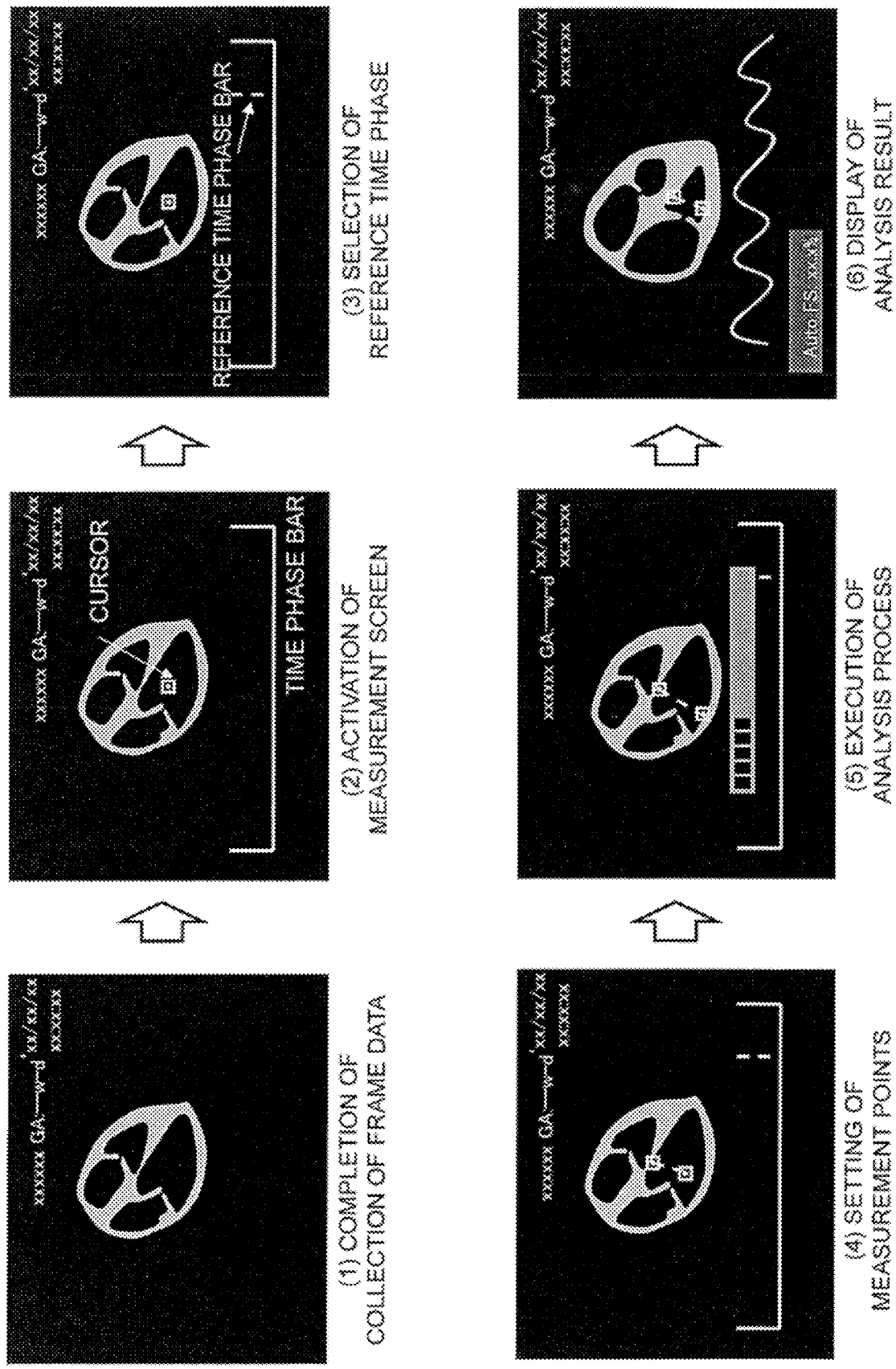
FIG. 2 is a diagram for explaining a specific example of diagnosis using the ultrasound diagnostic apparatus of FIG. 1.

FIG. 2 is a diagram for explaining a specific example of diagnosis using the ultrasound diagnostic apparatus of FIG. 1. FIG. 2 shows a specific example of a display image formed by the display image former 70 and displayed on the display 72, in a diagnosis related to a heart of a fetus which is one specific example of the diagnosis target.

In the diagnosis related to the heart of the fetus, a user such as a doctor or an inspection professional, for example, causes a transmission and reception surface of the probe 10 to contact a body surface (for example, at abdomen) of a pregnant woman (mother's body), and adjusts a position and an orientation of the probe 10 such that an ultrasound image (tomographic image) related to the heart of the fetus is displayed on the display 72. In a state where a desired tomographic image is obtained, frame data of a plurality of time phases related to the heart of the fetus are collected. An image exemplified in (1) of FIG. 2 is a specific example of the display image when collection of the frame data is completed, and shows a tomographic image of the heart of the fetus. The collected frame data of the plurality of time phases are stored in the data storage 22.

When the frame data are collected, a measurement screen is activated. An image exemplified in (2) of FIG. 2 is a specific example of a display image showing a measurement screen (for example, immediately after activation). In the specific example shown in (2) of FIG. 2, in the tomographic image related to the heart of the fetus shown on the measurement screen, a cursor for designated a measurement point is displayed, and a time phase bar is displayed at a lower side of the tomographic image. For example, a time phase bar showing, in a left-and-right direction, a range of the time phases corresponding to the collected frame data of the plurality of time phases is displayed.

Next, a reference time phase is selected by the user such as the doctor or the inspection professional. An image exemplified in (3) of FIG. 2 is a specific example of a display image which is used when the reference time phase is selected. For example, as in the specific example exemplified in (3) of FIG. 2, a reference time phase bar is displayed at a position corresponding to the reference time phase in the time phase range shown by the time phase bar. For example, when the user manipulates the manipulation device 80 to move the reference time phase bar to the left and to the right, a tomographic image based on the frame data of the time phase corresponding to the position of the reference time phase bar is displayed. The user such as the doctor or the inspection professional, for example, checks the tomographic image while moving the reference time phase bar to the left and to the right, to select the reference time phase in which a desired tomographic image can be obtained. For example, the reference time phase is set at a time phase corresponding to or which is close to a diastole of the heart of the fetus.

When the reference time phase is selected, a measurement point is set by the user such as the doctor or the inspection professional. An image exemplified in (4) of FIG. 2 is a specific example of a display image which is used when the measurement point is set. The ultrasound diagnostic apparatus of the specific example of FIG. 1 has, for example, various measurement functions related to the heart of the fetus. One specific example of the measurement functions is measurement of a fractional shortening (FS) (FS measurement). In the FS measurement, two measurement points are set for the heart of the fetus (for example, in the left ventricle). For example, each of the two measurement points is set at an intima surface of the heart (boundary surface between a heart wall and a lumen). The user such as the doctor or the inspection professional manipulates the manipulation device 80 to designate two locations where the FS measurement is to be executed. Based on the location designated by the user, for example, the measurement point setter 52 sets the measurement point. With this process, for example, two measurement points are set for the tomographic image of the reference time phase. For example, after one measurement point is set, the other measurement point is set.

When the two measurement points are set, an analysis process is executed. An image exemplified in (5) of FIG. 2 is a specific example of a display image displayed on the display 72 during execution of the analysis process. For example, as in the specific example shown in (5) of FIG. 2, a display form showing a progress status of the analysis process (such as a bar showing development of the process) may be displayed.

When the analysis process is completed, a result of the analysis process is displayed. An image exemplified in (6) of FIG. 2 is a specific example of a display image showing the analysis result of the FS measurement. For example, as in the specific example shown in (6) of FIG. 2, an FS measurement value obtained as the analysis result of the FS measurement is displayed as a numerical value (such as "xx.x %") or the like. Alternatively, a waveform or the like showing a distance between the two measurement points which changes over the plurality of time phases may be displayed.

Figure 3:
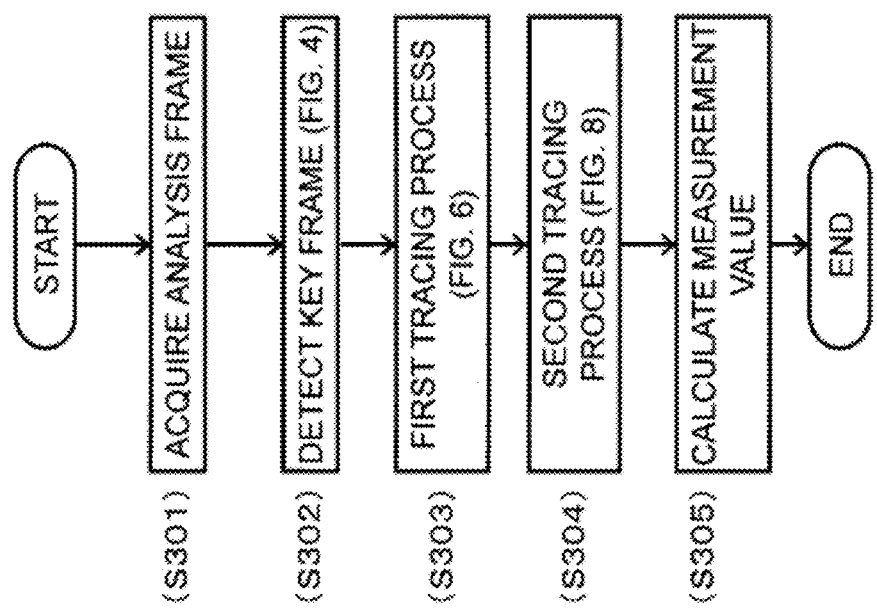
FIG. 3 is a diagram showing a specific example of an analysis process executed by the ultrasound diagnostic apparatus of FIG. 1.

FIG. 3 is a diagram (flowchart) showing a specific example of the analysis process executed by the ultrasound diagnostic apparatus of FIG. 1. For example, when two measurement points are set in the specific example of the diagnosis shown in FIG. 2 (for example, with the setting of the second measurement point as a trigger), the analysis process exemplified in FIG. 3 is started.

First, an analysis frame is acquired (S301). The analysis frame acquisition unit 30 acquires a plurality of frame data to be a target of analysis from among a plurality of frame data stored in the data storage 22. The analysis frame acquisition unit 30 acquires, for example, as the analysis target, a plurality of frame data in a predefined period including the reference time phase selected by the user such as the doctor or the inspection professional. For example, a plurality of frame data included in a period, centered at the reference time phase, and from a preset number of seconds before the reference time phase to the preset number of seconds after the reference time phase, may be selected as the analysis target.

Next, a key frame is detected (S302). The key frame detector 40 detects a plurality of key frames corresponding to distinct time phases from among the plurality of frame data which are the analysis target. The key frame detector 40 detects, for example, in the diagnosis related to the heart of the fetus, peak time phases corresponding to the diastole and a systole as the distinct time phases, using a heartbeat waveform of the fetus obtained based on the plurality of frame data which are the analysis target.

Figure 4:
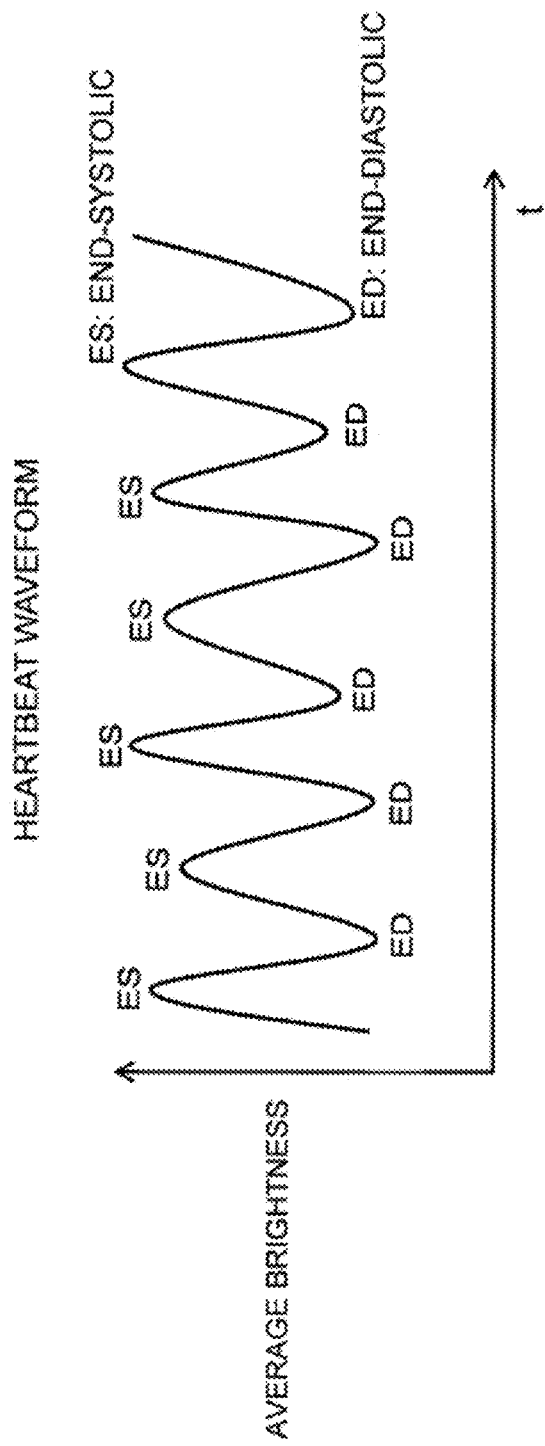
FIG. 4 is a diagram showing a specific example of a heartbeat waveform.

FIG. 4 is a diagram showing a specific example of the heartbeat waveform. FIG. 4 shows the heartbeat waveform showing a time axis (an axis of the plurality of time phases) on a horizontal axis, and an average brightness which is an amplitude on a vertical axis.

In obtaining the heartbeat waveform of FIG. 4, first, a region of interest is set with respect to the heart of the fetus in the tomographic image based on the frame data. For example, the region of interest is set according to the user manipulation which is input through the manipulation device 80. The user such as the doctor or the inspection professional manipulates the manipulation device 80, for example, while viewing the tomographic image displayed on the display 72, to set a position and a size of the region of interest so that the heart of the fetus (in particular, the heart wall) is included in the region. Alternatively, for example, a region of interest centered at one of the two measurement points used in the FS measurement may be set. Alternatively, the ultrasound diagnostic apparatus of FIG. 1 may set the region of interest on the heart of the fetus by analyzing an image state in the tomographic image.

The region of interest is set, for example, at a location where the motion of the heart of the fetus can be easily detected. Specifically, for example, the user sets the position and the size of the region of interest so that the heart portion of the fetus having a relatively high brightness is included in the region. Alternatively, the ultrasound diagnostic apparatus of FIG. 1 may judge the heart portion of the fetus having the relatively high brightness by, for example, an image analyzing process such as a binarization process, and may determine the position and the size of the region of interest. Alternatively, the region of interest may be set at another location where the motion of the heart of the fetus can be easily detected.

When the region of interest is set, the key frame detector 40 generates the heartbeat waveform of the fetus based on the image data (frame data) in the region of interest. The key frame detector 40 calculates, for example, an average brightness (an average of brightness values) in the region of interest based on the image data in the region of interest, and calculates an average brightness for each time phase over a plurality of time phases with a plurality of frame data which are the analysis target as a processing target, to generate the heartbeat waveform shown in FIG. 4.

Because the heart of the fetus periodically expands and contracts, the average brightness changes with the expansion-contraction motion, and the heartbeat waveform as shown in, for example, the specific example of FIG. 4 is obtained. For example, when the region of interest is set to include the heart wall, with the contraction of the heart, a ratio of a cardiac muscle in the region of interest becomes high and the average brightness is increased with the contraction of the heart, and a ratio of the lumen in the region of interest becomes high and the average brightness is reduced with the expansion of the heart. With this process, as shown in the specific example of FIG. 4, the heartbeat waveform is obtained in which the average brightness periodically changes and an end-diastole ED (peak time phase corresponding to the diastole) and an end-systole ES (peak time phase corresponding to the systole) are periodically repeated.

The key frame detector 40 detects, as the plurality of key frames, a plurality of frames corresponding to, for example, the time phase of the end-diastole ED, from among the plurality of frame data which are the analysis target. Alternatively, the key frame detector 40 may detect a plurality of frames corresponding to the time phase of the end-systole ES as the plurality of key frames, or a plurality of frames corresponding to both time phases of the end-diastole ED and the end-systole ES as the plurality of key frames.

Referring back to FIG. 3, when a plurality of key frames are detected, a tracing process is executed, targeted to one or more sites of interest in the tissue which is the diagnosis target. For example, the trace processor 50 executes a first tracing process (S303) and a second tracing process (S304). In the second tracing process, the trace processor 50 derives an amount of temporal change at each coordinate of interest of a plurality of coordinates of interest which are spatially fixed in the frame data over a plurality of time phases.

Then, a measurement value is calculated (S305). The measurement value calculator 60 calculates the measurement value based on, for example, a trace result of the site of interest by the trace processor 50. For example, in the measurement (FS measurement) of the fractional shortening (FS) related to the heart of the fetus, the FS value described in JP 5918325 B may be calculated from the trace result of two measurement points which are set for the heart of the fetus. When the measurement value is calculated, the analysis process exemplified in FIG. 3 is completed.

Figure 5:
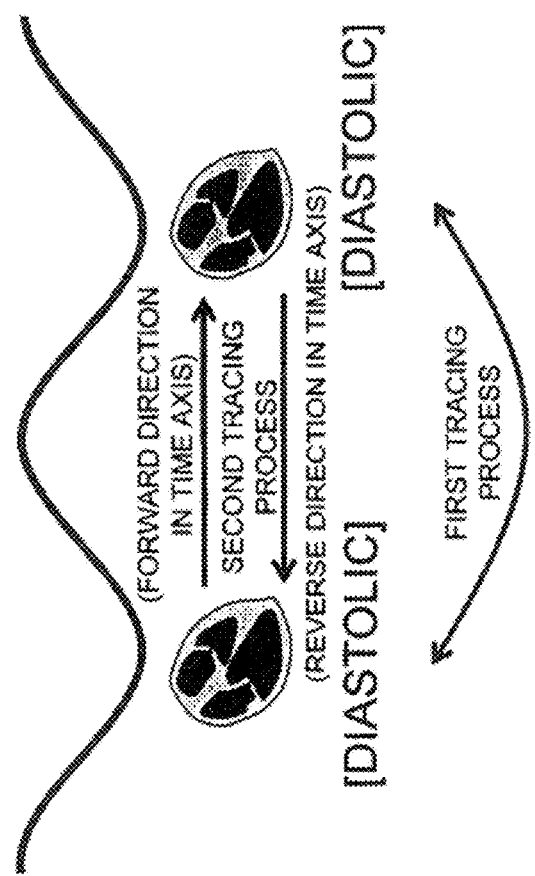
FIG. 5 is a diagram showing a specific example of a tracing process executed by the ultrasound diagnostic apparatus of FIG. 1.

FIG. 5 is a diagram showing a specific example of the tracing process executed by the ultrasound diagnostic apparatus of FIG. 1. FIG. 5 exemplifies an overview of the tracing process executed in the diagnosis related to the heart of the fetus. In the diagnosis related to the heart of the fetus, the tracing process is executed with each of the two measurement points as a site of interest.

The trace processor 50 executes the first tracing process to trace the site of interest, with the plurality of key frames as the processing target. The trace processor 50 executes the tracing process, for example, with the plurality of frame data corresponding to the time phase of the diastole (end-diastole ED) as the processing target, and with each of the two measurement points as the site of interest.

In addition, the trace processor 50 executes the second tracing process to trace a motion of each site of interest in a trace period from one of two adjacent key frames to the other of the adjacent key frames. The trace processor 50 executes the tracing process, for example, with a plurality of frame data in a period from a time phase of the diastole to a time phase of a diastole adjacent to this diastole as the processing target, and with each of the two measurement points as the site of interest.

In the second tracing process, there may be executed a tracing process to progress the process in a reverse direction on the time axis from the tracing process to progress the process in a forward direction of the time axis. For example, the trace processor 50 starts the process from frame data corresponding to the diastole of an earlier time phase (having a smaller value of the time phase) of the two adjacent diastoles and executes the tracing process in the forward direction to progress the process in the forward direction on the time axis to the frame data corresponding to the diastole of a later time phase (having a larger value of the time phase). In addition, for example, the trace processor 50 starts the process from the frame data corresponding to the diastole of the later time phase (having a larger value of the time phase) of the two adjacent diastoles, and executes the tracing process in the reverse direction to progress the process in the reverse direction on the time axis to the frame data corresponding to the diastole of the earlier time phase (having a smaller value of the time phase). The trace processor 50 then may obtain the trace result of the second tracing process based on, for example, the trace result obtained by the tracing process in the forward direction and the trace result obtained by the tracing process in the reverse direction.

The overview of the first tracing process and the second tracing process exemplified in FIG. 5 has been described. Specific examples of the first tracing process and the second tracing process will now be described.

Figure 6:
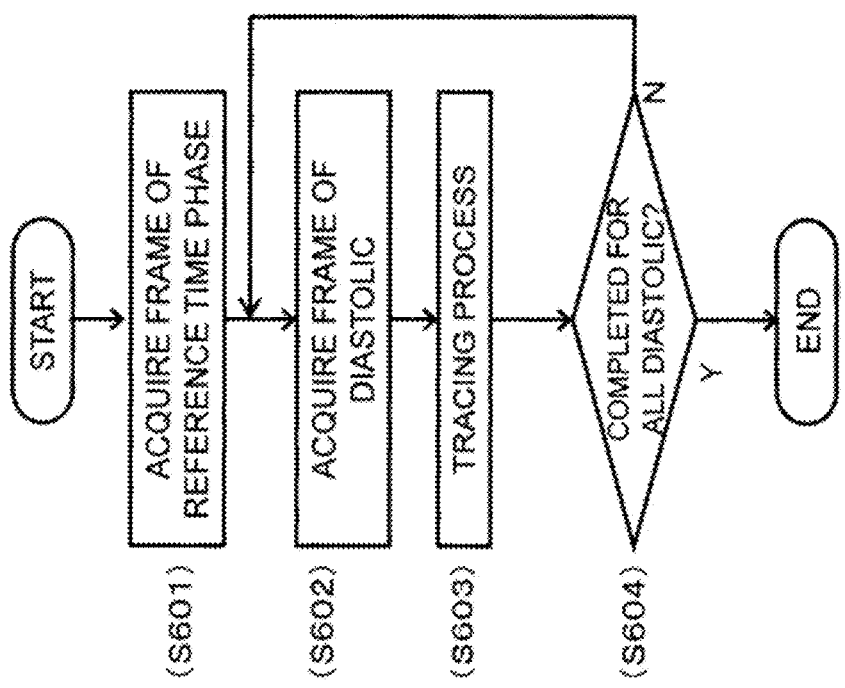
FIG. 6 is a diagram showing a specific example of a first tracing process.

FIG. 6 is a diagram (flowchart) showing a specific example of the first tracing process. FIG. 6 shows a specific example of the first tracing process executed in the step of S303 of FIG. 3. For example, with the completion of the detection process of the key frame executed in S302 of FIG. 3 as a trigger, the first tracing process exemplified in FIG. 6 is started.

When the first tracing process exemplified in FIG. 6 is started, first, the frame of the reference time phase is acquired (S601). The trace processor 50 acquires frame data corresponding to the reference time phase selected by the user, from among the plurality of frame data (frame data acquired in S301 of FIG. 3) which are the analysis target, for example. In the frame data corresponding to the reference time phase, measurement points are set by the measurement point setter 52. For example, in the case of the FS measurement, two measurement points are set for the heart of the fetus in the frame data of the reference time phase.

Next, a frame of the diastole is acquired (S602). The trace processor 50 acquires frame data corresponding to the time phase of the diastole (end-diastole ED) detected by the key frame detector 40, from among the plurality of frame data which are the analysis target, for example.

Then, the tracing process is executed (S603). The trace processor 50 searches for a movement destination of each of the two measurement points from the reference time phase, with the frame data corresponding to the reference time phase acquired in S601 and the frame data corresponding to the time phase of the diastole acquired in S602 as processing targets.

The steps of S602 an S603 are executed for all diastoles (end-diastoles ED) included in the plurality of frame data which are the analysis target. When it is confirmed that the process targeted to all of the diastoles is completed (S604), the first tracing process exemplified in FIG. 6 is completed.

In the first tracing process, for example, a template corresponding to each of the two measurement points is set in the frame data corresponding to the reference time phase, and a process (template matching) is executed to search for a position which is similar to the template corresponding to each of the two measurement points in the frame data corresponding to the time phase of the diastole, by a correlation calculation. With this process, there is derived a position (coordinate) of the movement destination in the frame data corresponding to the time phase of the diastole, related to the two measurement points in the frame data corresponding to the reference time phase.

Alternatively, in the first tracing process, a tracing process may be executed using a plurality of auxiliary points as described in JP 5918325 B. For example, in the frame data corresponding to the reference time phase, a plurality of auxiliary points (a1~a4) corresponding to one of the two measurement points, measurement point A, are set, and a plurality of auxiliary points (b1~b4) corresponding to the other of the two measurement points, measurement point B, are set. A tracing process may be executed with the measurement point A and the plurality of auxiliary points (a1~a4) as trace points, and the motion of the measurement point A may be traced using a plurality of trace results obtained from the plurality of trace points. In addition, a tracing process may be executed with the measurement point B and the plurality of auxiliary points (b1~b4) as trace points, and the motion of the measurement point B may be traced using a plurality of trace results obtained from the plurality of trace points.

Alternatively, in the first tracing process, a standardization process may be executed, for reducing a brightness difference between the frame data corresponding to the reference time phase and the frame data corresponding to the time phase of the diastole.

Figure 7:
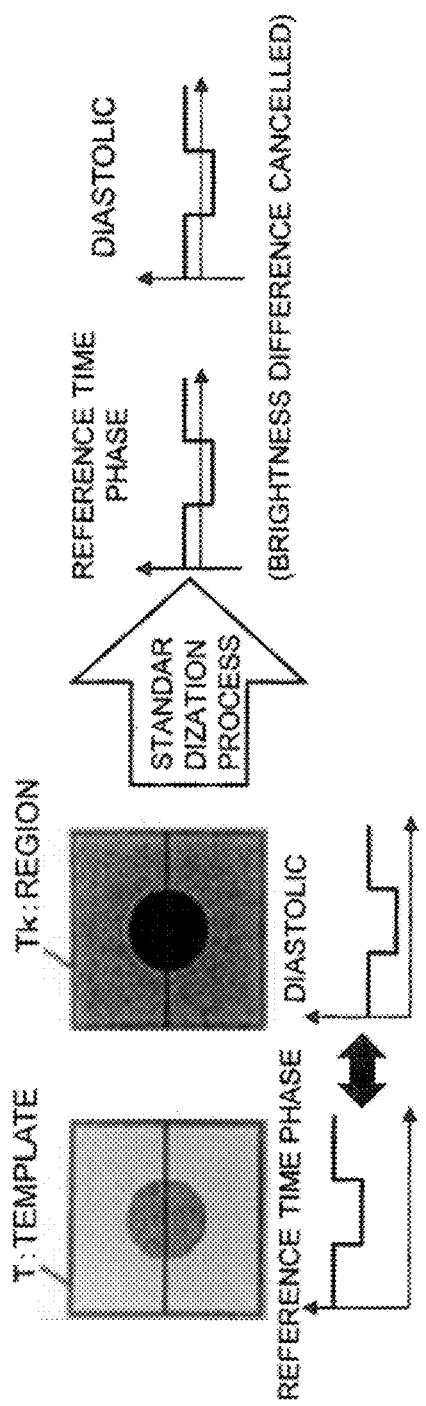
FIG. 7 is a diagram showing a specific example of a standardization process.

FIG. 7 is a diagram showing a specific example of the standardization process. In the first tracing process, because the reference time phase and the time phase of the diastole which are separated in time from each other are set as the processing targets, a relatively large brightness difference may be caused between the frame data corresponding to the reference time phase and the frame data corresponding to the time phase of the diastole, due to influences of shadow or the like generated during the transmission and reception of the ultrasound, for example. In consideration of this, the standardization process exemplified in FIG. 7 is executed, in order to reduce or cancel the brightness difference.

In the specific example of the standardization process shown in FIG. 7, for example, after reduction or cancellation of a difference between the brightness in the template which is set for the frame data corresponding to the reference time phase and the brightness of a region Tk corresponding to a template T in the frame data corresponding to the time phase of the diastole, a correlation calculation is executed between the template T and the region Tk. For example, brightness values in at least one of the template T and the region Tk are corrected such that a difference between an average value of the brightness in the template T and an average value of the brightness in the region Tk is 0 (zero).

With the execution of the standardization process, instability of the tracing process due to the brightness difference can be reduced or resolved, and a stable first tracing process can be realized.

Figure 8:
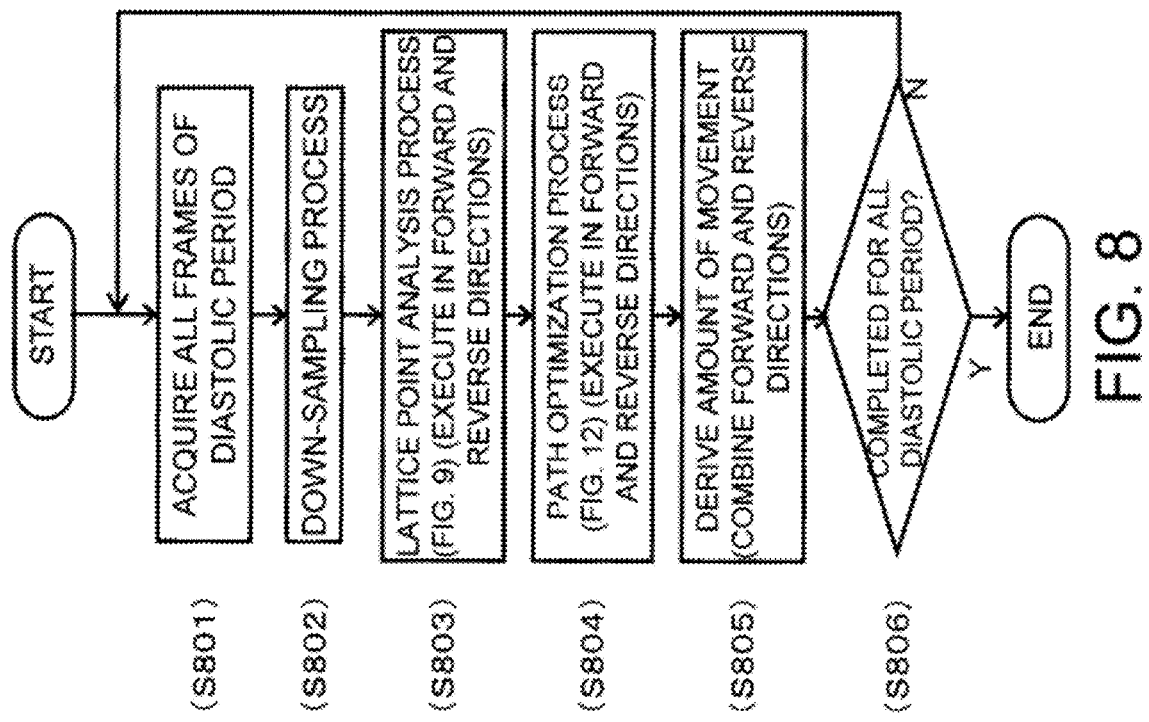
FIG. 8 is a diagram showing a specific example of a second tracing process.

FIG. 8 is a diagram (flowchart) showing a specific example of the second tracing process. FIG. 8 shows a specific example of the second tracing process executed in the step of S304 of FIG. 3. For example, with the completion of the first tracing process executed in the step of S303 as a trigger, the second tracing process exemplified in FIG. 8 is started.

When the second tracing process exemplified in FIG. 8 is started, first, all frames of the diastolic period are acquired (S801). The trace processor 50 acquires, for example, frame data of a plurality of time phases from a time phase corresponding to one of two adjacent diastoles (end-diastoles ED) to a time phase corresponding to the other of the adjacent diastoles, from among the plurality of frame data which are the analysis target.

Next, a down-sampling process is executed (S802). The trace processor 50 executes, for example, the down-sampling process on the frame data of the plurality of time phases acquired in S801, to reduce a number of pixels corresponding to the frame data of each time phase. With this process, a load of the subsequent processes (for example, processes from S803 to S805) can be reduced, and the processing speed at the subsequent processes can be improved. Alternatively, the down-sampling process may be omitted.

Next, a lattice point analysis process (S803) and a path optimization process (S804) are executed, and an amount of movement is derived based on results of these processes (S805). The processes from S801 to S805 are executed for all diastolic periods (all combinations of two adjacent diastoles) included in the plurality of frame data which are the analysis target, and, when it is confirmed that the process targeted to all diastoles is completed (S806), the second tracing process exemplified in FIG. 8 is completed.

Figure 9:
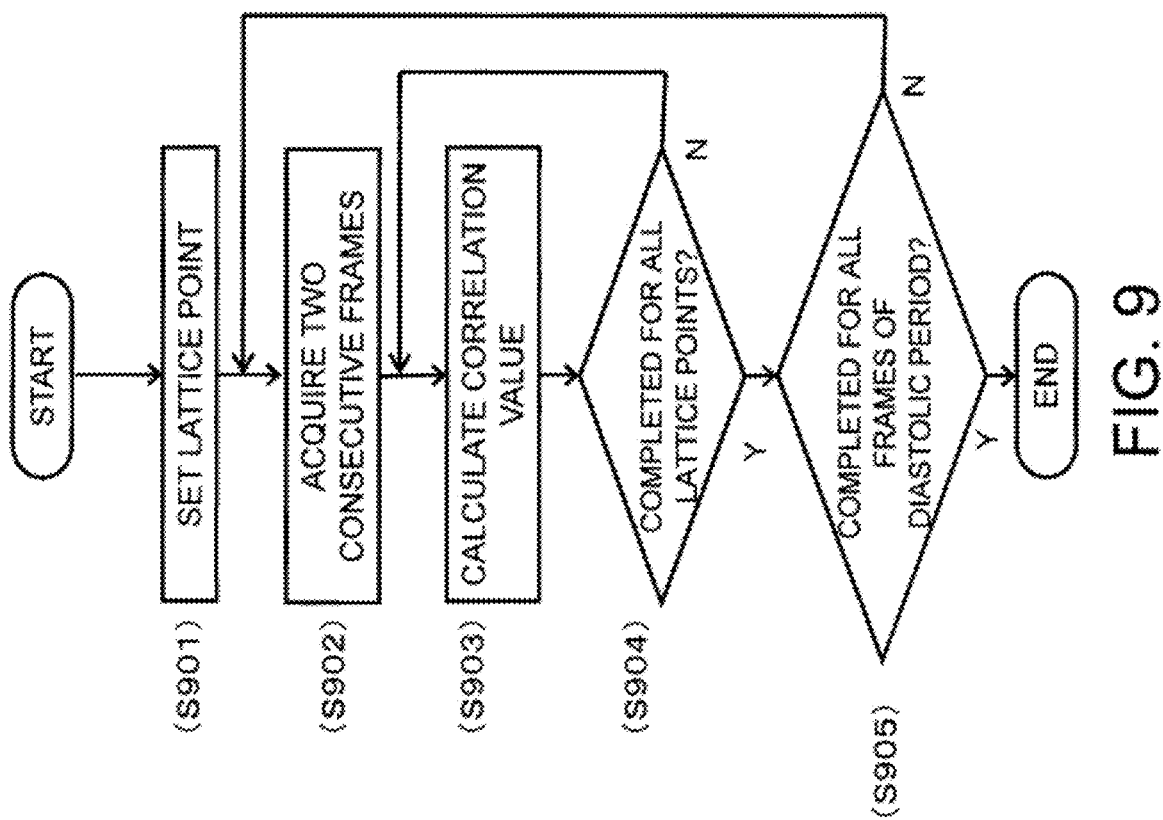
FIG. 9 is a diagram showing a specific example of a lattice point analyzing process.

FIG. 9 is a diagram (flowchart) showing a specific example of the lattice point analysis process. FIG. 9 shows a specific example of the lattice point analysis process executed in the step of S803 of FIG. 8. For example, with the completion of the down-sampling process executed in the step of S802 of FIG. 8 as a trigger, the lattice point analysis process exemplified in FIG. 9 is started.

When the lattice point analysis process exemplified in FIG. 9 is started, first, setting of lattice points is executed (S901). The trace processor 50 sets, for example, a plurality of lattice points as specific examples of the plurality of coordinates of interest which are spatially fixed in the frame data over the plurality of time phases.

Figure 10:
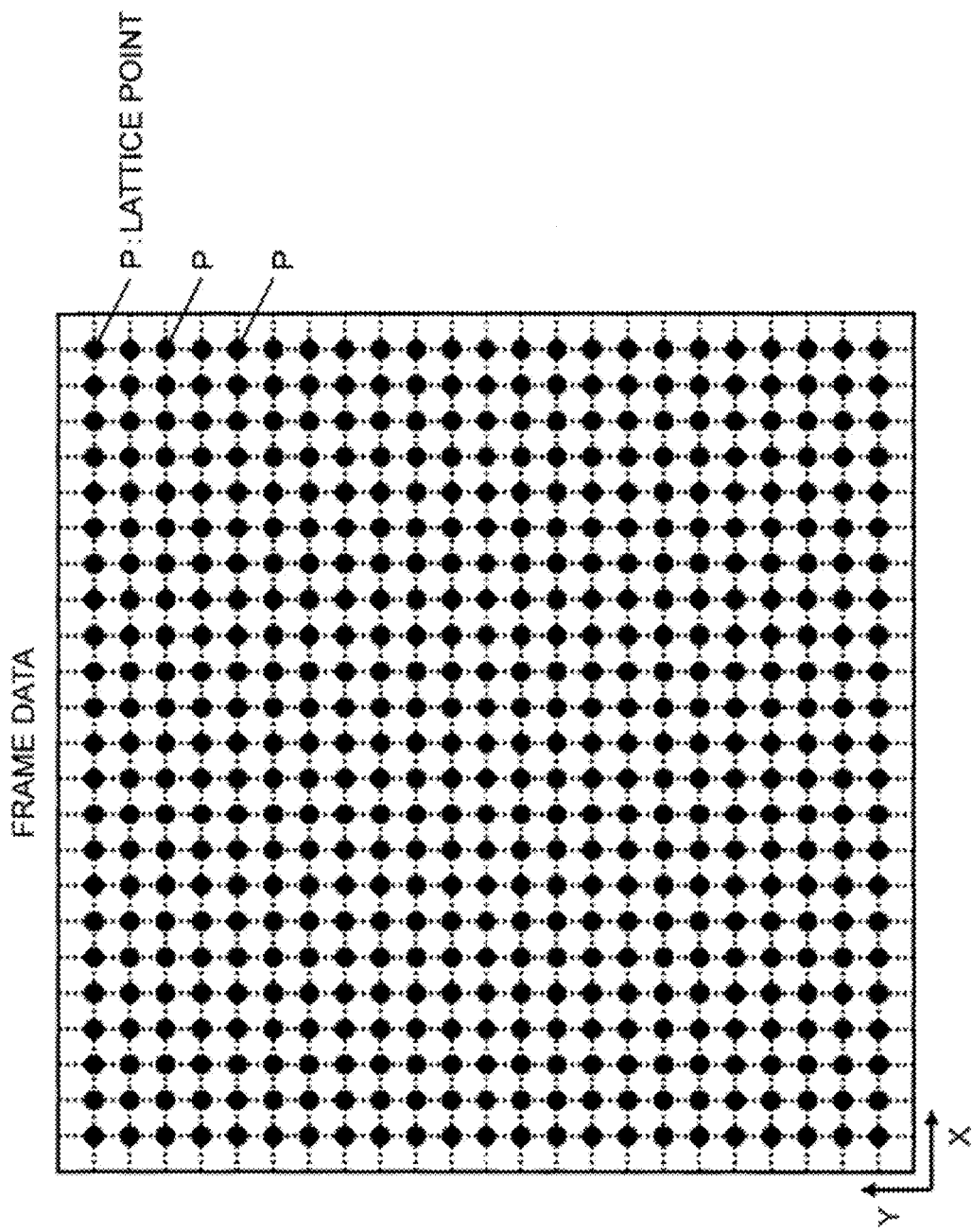
FIG. 10 is a diagram showing a specific example of a plurality of lattice points.

FIG. 10 is a diagram showing a specific example of the plurality of lattice points. FIG. 10 shows a specific example of the plurality of lattice points (P) which are set for the frame data. In the specific example of FIG. 10, the plurality of lattice points are set, for example, with a certain interval in each direction of an X-axis direction and a Y-axis direction. For example, each lattice point may be set at a position of each pixel (each data) of a plurality of pixels (plurality of data) forming the frame data.

While FIG. 10 shows a specific example in which the frame data has a quadrangular shape, the plurality of lattice points may alternatively be arranged according to the shape of the frame data. For example, even when the frame data has a shape different from the quadrangular shape, the lattice points may be set at positions of each pixel (each data) of the plurality of pixels (plurality of data) forming the frame data.

Referring back to FIG. 9, when the plurality of lattice points are set, two consecutive frames are acquired (S902). The trace processor 50 acquires two frame data corresponding to two consecutive time phases from among the frame data of the plurality of time phases acquired in S801 (FIG. 8), for example.

Next, a calculation of a correlation value is executed (S903). For example, the trace processor 50 generates a correlation value map showing a distribution of the correlation values for each lattice point, by a correlation calculation between time phases based on two frame data acquired in S902.

The calculation of the correlation value (generation of the correlation value map) is repeatedly executed until calculation for all lattice points is completed (S904). The processes from S902 to S904 are executed for all of the frame data corresponding to two consecutive time phases included in the frame data of the plurality of time phases acquired in S801 (FIG. 8), and, when it is confirmed that the process targeted to all frame data is completed (S905), the lattice point analysis process exemplified in FIG. 9 is completed.

Figure 11:
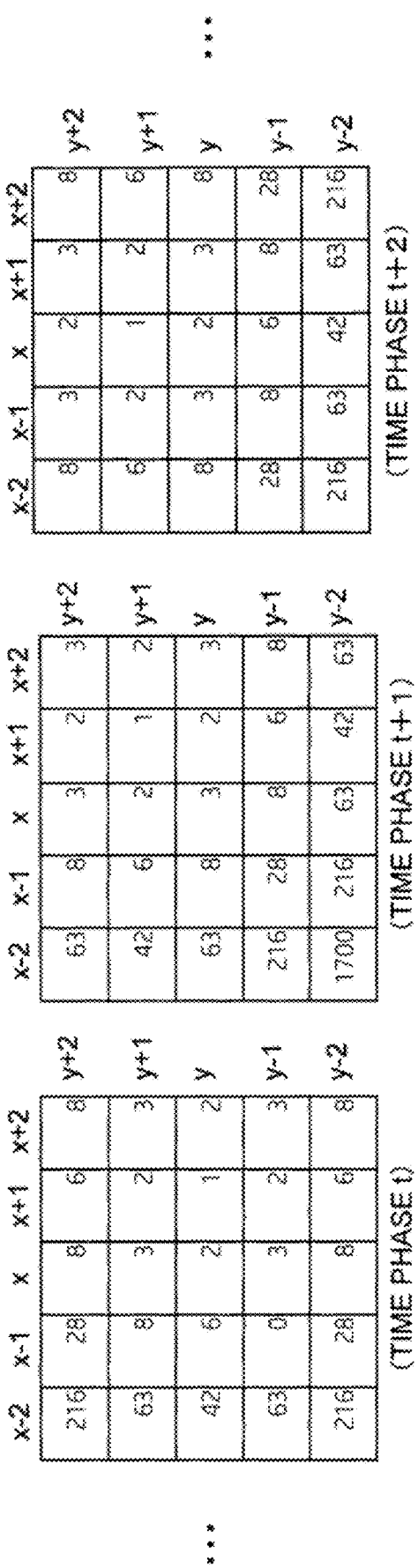
FIG. 11 is a diagram showing a specific example of a correlation value map.

FIG. 11 is a diagram showing a specific example of a correlation value map. FIG. 11 shows, as a specific example of the correlation value map obtained by the lattice point analysis process exemplified in FIG. 9, a correlation value map for a lattice point (x, y) at a position of a coordinate (x, y).

In the specific example shown in FIG. 11, the correlation value map of a time phase t is derived, for example, based on two frame data corresponding to a time phase t−1 and the time phase t. For example, a correlation value map of the time phase t is generated by a correlation calculation based on data corresponding to the lattice point (x, y) in the frame data of the time phase t−1 (for example, a plurality of data in a predetermined range centered at the lattice point (x, y)) and data corresponding to a plurality of lattice points centered at the lattice point (x, y) in the frame data of the time phase t (for example, a plurality of data in a predetermined range centered at each lattice point).

For example, when the correlation value of the data corresponding to the lattice point (x, y) in the frame data of the time phase t−1 and the data corresponding to a lattice point (x+1, y) in the frame data of the time phase t is "1," the correlation value corresponding to the lattice point (x+1, y) in the correlation value map of the time phase t is set to "1," as shown in the specific example of FIG. 11.

Further, in the specific example shown in FIG. 11, the correlation value map of the time phase t+1 is derived, for example, based on two frame data corresponding to the time phase t and the time phase t+1, and the correlation value map of a time phase t+2 is derived, for example, based on two frame data corresponding to the time phase t+1 and the time phase t+2.

Alternatively, for example, the correlation value map of the time phase t may be derived based on two frame data corresponding to the time phase t and the time phase t+1, the correlation value map of the time phase t+1 may be derived based on two frame data corresponding to the time phase t+1 and the time phase t+2, and the correlation value map of the time phase t+2 may be derived based on two frame data corresponding to the time phase t+2 and a time phase t+3.

In the specific example shown in FIG. 11, a sum of squared difference (SSD) is used as the correlation value, with a smaller value of the SSD indicating a higher similarity. Alternatively, in obtaining the correlation value map, a correlation value other than the SSD may be used. Alternatively, a correlation value having a higher value for a higher similarity may be used.

Further, in the specific example shown in FIG. 11, a correlation value map of a size corresponding to 25 lattice points centered at the lattice point (x, y) is shown, but the size of the correlation value map (range of the lattice points) is not limited to the specific example exemplified in FIG. 11. For example, a correlation value map of a size corresponding to less than or equal to 25 lattice points may be generated, or a correlation value map of a size corresponding to greater than or equal to 25 lattice points may be generated.

Figure 12:
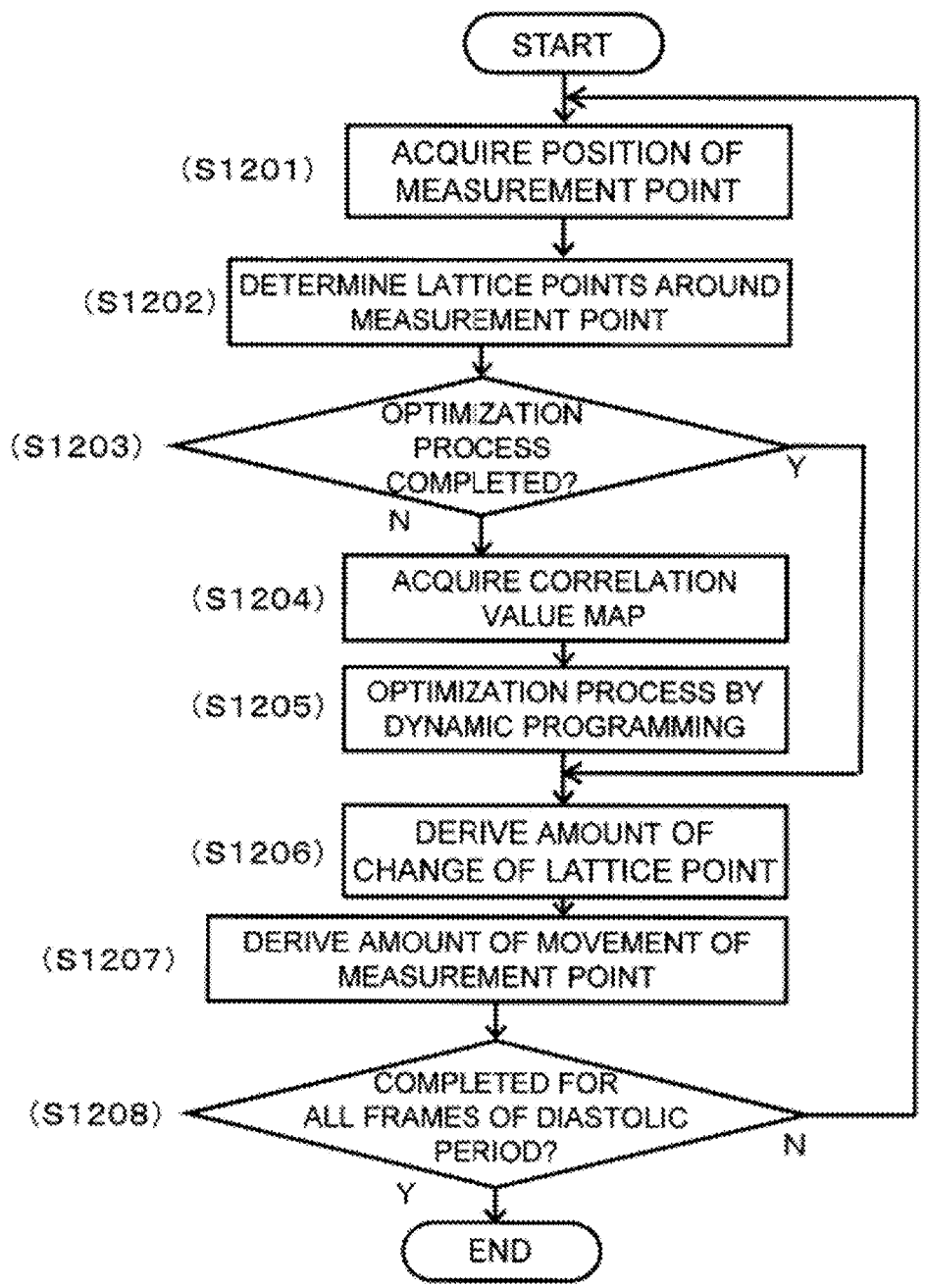
FIG. 12 is a diagram showing a specific example of a path optimization process.

FIG. 12 is a diagram (flowchart) showing a specific example of the path optimization process. FIG. 12 shows a specific example of the path optimization process executed in the step of S804 of FIG. 8. For example, with a completion of the lattice point analysis process executed in the step of S803 of FIG. 8 as a trigger, the path optimization process exemplified in FIG. 12 is started.

When the path optimization process exemplified in FIG. 12 is started, first, a position of a measurement point is acquired (S1201). The trace processor 50 acquires, for example, positions (coordinate values) of the measurement points in the frame data corresponding to two diastoles (end-diastoles ED) included in the plurality of frame data acquired in S801 (FIG. 8). The measurement point in the frame data corresponding to the diastole is already traced by the first tracing process (refer to FIGS. 5 and 6). In the FS measurement, for example, the coordinate values of the two measurement points related to the heart of the fetus are acquired by the trace processor 50. When there are a plurality of measurement points, the processes from S1202 to S1207 described below are executed for each measurement point.

When the position of the measurement point is acquired, lattice points around the measurement point are determined (S1202). The trace processor 50 selects, for example, a plurality of lattice points around each measurement point. For example, four lattice points surrounding each measurement point may be selected.

Next, it is checked whether or not an optimization process is completed (S1203). The trace processor 50 checks whether or not the optimization process is completed for, for example, all of the plurality of lattice points determined in S1202.

When there is at least one lattice point for which the optimization process is not completed, processes of S1204 and S1205 are executed. Specifically, the correlation value map is acquired (S1204), and the optimization process by dynamic programming is executed (S1205). Then, an amount of change of the lattice point is derived (S1206). On the other hand, when the optimization process is already completed for all of the plurality of lattice points determined in S1202, the processes of S1204 and S1205 are skipped, and the amount of change of the lattice point is derived (S1206).

Figure 13:
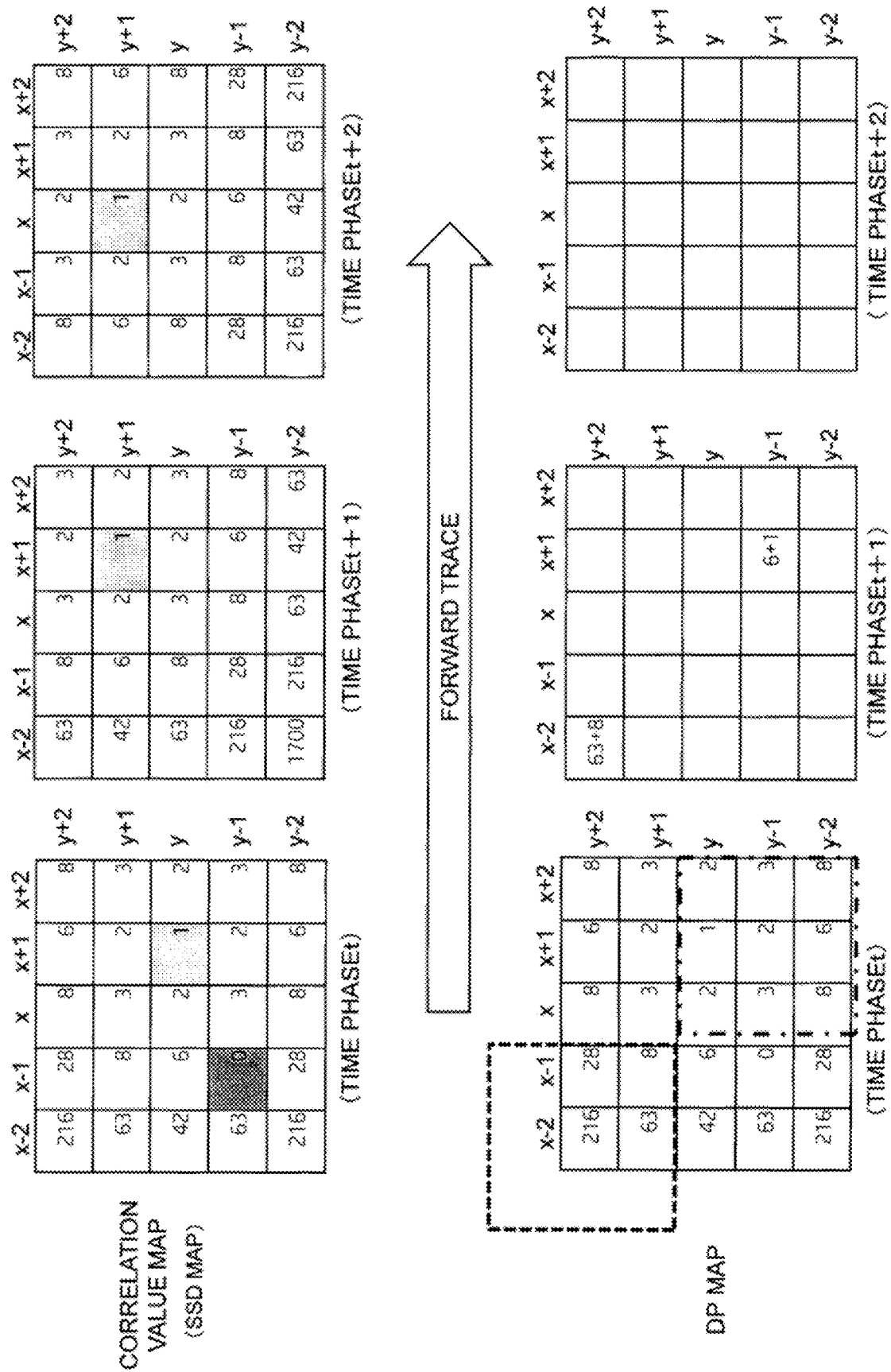
FIG. 13 is a diagram showing a specific example of forward trace of dynamic programming.
Figure 15:
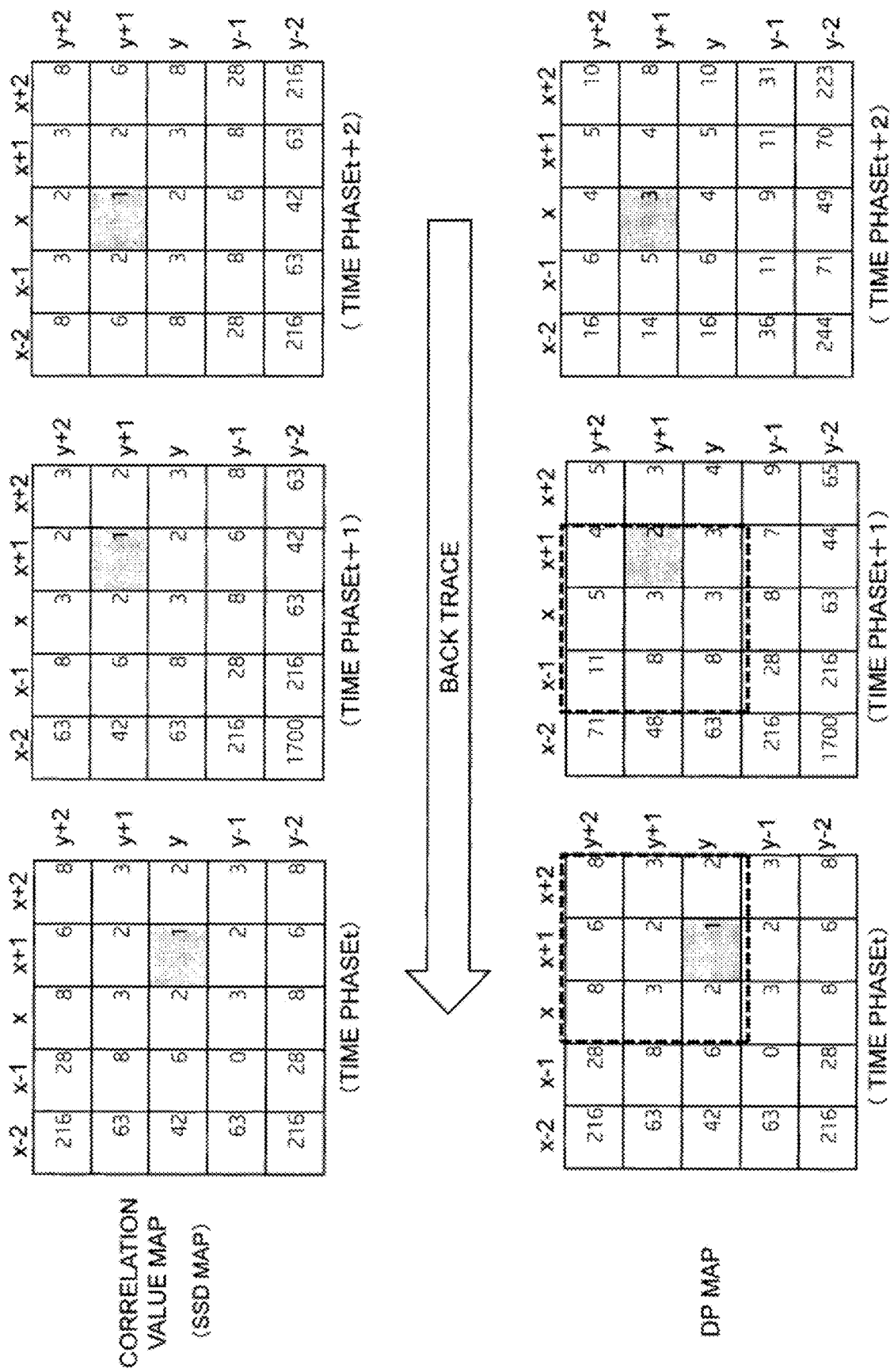
FIG. 15 is a diagram showing a specific example of back trace of dynamic programming.

FIGS. 13 to 15 are diagrams for explaining a specific example of the optimization process by the dynamic programming. The trace processor 50 applies the dynamic programming, for example, on the correlation value map generated in the lattice point analysis process.

FIG. 13 is a diagram showing a specific example of forward trace of the dynamic programming. An SSD map shown in FIG. 13 is a specific example of the correlation value map obtained by the lattice point analysis process exemplified in FIG. 9, and is a correlation value map (FIG. 11) for the lattice point (x, y) at the position of the coordinate (x, y).

There may be cases where, in the correlation value map, a specifically similar position is present due to, for example, influences of noise. For example, in the specific example of FIG. 13, when the actual change destination of the lattice point (x, y) in the correlation value map of the time phase t is a coordinate (x+1, y), there may be a case where a correlation value of a coordinate (x−1, y−1) which is "0" is smaller than the correlation value of the coordinate (x+1, y) which is "1." In this case, if the change destination of the lattice point (x, y) is to be determined based solely on the correlation value map of the time phase t, there is a possibility of erroneous recognition of the coordinate (x−1, y−1) which is a specifically generated similar position due to influences of noise or the like, for example, as the change destination of the lattice point (x, y), in place of the actual change destination which is the coordinate (x+1, y).

In order to resolve (or significantly reduce) such an erroneous recognition, the trace processor 50 applies the dynamic programming in the time axis direction on the correlation value maps of a plurality of time phases. The trace processor 50 first executes forward trace on the correlation value maps of the plurality of time phases, to generate DP maps of the plurality of time phases. For example, based on the following formula, the DP map DPMap(x, y, n) of a time phase n is generated from the correlation value map of the time phase n, SSDMap(x, y, n).

$$DPMap(x,y,n)=SSDMap(x,y,n)+Min\{DPMap(x+i,y+j, n-1)\} \qquad \text{<Formula 1>}$$

wherein DPMap(x, y, 0)=SSDMap(x, y, 0)

FIG. 13 shows a specific example when i is set in "−1≤i≤1" and j is set in "−1≤j≤1" in Formula 1. In the specific example shown in FIG. 13, when the forward trace is started from the time phase t, first, the correlation value map of the time phase t is copied as is, and is used as the DP map of the time phase t. In the forward trace, a minimum value is searched from a nearby area of the DP map of one time phase earlier, and is added to the value of the correlation value map.

For example, for a correlation value of a coordinate (x−2, y+2) of the correlation value map of the time phase t+1, which is "63," a minimum value, which is 8, is searched from the nearby area (range of −1≤i≤1 and −1≤j≤1 shown by a broken-line quadrangle) of the coordinate (x−2, y+2) in the DP map of the time phase t which is one time phase earlier, and is added to the correlation value of "63." The sum, "63+8" is set as the value of the coordinate (x−2, y+2) in the DP map of the time phase t+1.

In addition, for example, for a correlation value of a coordinate (x+1, y−1) of the correlation value map of the tie phase t+1, which is "6," a minimum value, which is 1, is searched from the nearby area (range of −1≤i≤1 and −1≤j≤1 shown by a chain-line quadrangle) of the coordinate (x+1, y−1) in the DP map of the time phase t which is one time phase earlier, and is added to the correlation value of "6." The sum, "6+1" is set as the value of the coordinate (x+1, y−1) in the DP map of the time phase t+1.

The trace processor 50 executes the forward trace based on, for example, Formula 1 for all coordinates included in the correlation value map; that is, all coordinates included in the DP map, and over all time phases to be processed. With this process, for example, DP maps of a specific example as shown in FIG. 14 are obtained.

FIG. 14 is a diagram showing a specific example of the DP map. FIG. 14 shows DP maps from the time phase t to the time phase t+2 obtained by the forward trace targeted to the correlation value maps of FIG. 13. When the DP maps of the plurality of time phases are obtained by the forward trace, back trace is executed using these DP maps of the plurality of time phases.

FIG. 15 is a diagram showing a specific example of the back trace of the dynamic programming. The DP maps shown in FIG. 15 are DP maps from the time phase t to the time phase t+2 obtained by the forward trace targeted to the correlation value maps of FIG. 13, and are DP maps shown in FIG. 14.

The back trace is started from the DP map of a final time phase which is generated at last. In the back trace, first, a minimum value is searched in the DP map of the final time phase, and then, a minimum value is searched in the nearby area of the DP map of one time phase earlier than the final time phase. Further, a minimum value is searched in the nearby area of the DP map of one time phase earlier than this DP map, and the search of the minimum value is executed until the DP map which is first generated. In other words, compared to the forward trace, the back trace is executed in the reverse direction in the time axis.

In the specific example shown in FIG. 15, the back trace is started from the DP map of the time phase t+2 which is finally generated. The trace processor 50 first searches the minimum value in the DP map of the time phase t+2, and obtains a coordinate (x, y+1) as the search result. Next, the trace processor 50 searches a minimum value in the nearby area (range of −1≤i≤1 and −1≤j≤1 shown by a broken-line quadrangle) of the coordinate (x, y+1) in the DP map of the time phase t+1 which is one time phase earlier, and obtains a coordinate (x+1, y+1) as the search result. The trace processor 50 further searches a minimum value in the nearby area (range of −1≤i≤1 and −1≤j≤1 shown by a broken-line quadrangle) of the coordinate (x+1, y+1) in the DP map of the time phase t which is one time phase earlier, and obtains a coordinate (x+1, y) as the search result.

The coordinate thus obtained by the back trace is set as the change destination of the lattice point corresponding to the correlation value map. For example, in the specific example shown in FIG. 15, the coordinate (x+1, y) obtained in the DP map of the time phase t is set as the change destination of the lattice point (x, y) at the time phase t, the coordinate (x+1, y+1) obtained in the DP map of the time phase t+1 is set as the change destination of the lattice point (x, y) in the time phase t+1, and the coordinate (x, y+1) obtained in the DP map of the time phase t+2 is set as the change destination of the lattice point (x, y) at the time phase t+2.

As described above with reference to the specific examples shown in FIGS. 13 to 15, the trace processor 50 applies the dynamic programming in the time axis direction on the correlation value maps of the plurality of time phases. With this process, it becomes possible to resolve (or significantly reduce) the erroneous recognition of the change destination.

For example, when the change destination of the lattice point (x, y) is to be determined based solely on the correlation value map of the time phase t exemplified in FIG. 13, there is a possibility of erroneous recognition of the coordinate (x−1, y−1) which is a similar position, as the change destination of the lattice point (x, y). On the contrary, with the application of the dynamic programming in the time axis direction, as exemplified in FIG. 15, it is possible to identify the coordinate (x+1, y), which is the actual change destination, as the change destination of the lattice point (x, y) at the time phase t.

When the change destination of the lattice point is identified by applying the dynamic programming in the time axis direction, an amount of change of the lattice point is derived (S1206 of FIG. 12). The trace processor 50 sets, for example, a change of coordinate from the lattice point to the change destination of the lattice point as an amount of change of the lattice point. For example, a vector quantity having the position of the lattice point as a starting point and the position of the change destination of the lattice point as a termination point may be set as the amount of change of the lattice point. Alternatively, when the amount of change of the lattice point is derived, parabola fitting in the spatial direction may be used.

Figure 16:
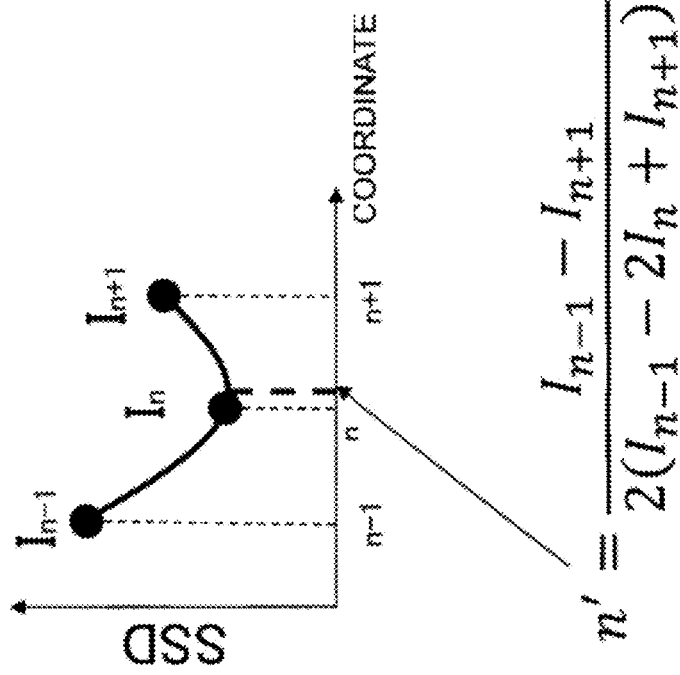
FIG. 16 is a diagram showing a specific example of parabola fitting.

FIG. 16 is a diagram showing a specific example of parabola fitting. FIG. 16 exemplifies a specific example in which the parabola fitting is applied during determination of the minimum point (coordinate corresponding to the minimum value) of the correlation value.

In the specific example of FIG. 16, of coordinates n−1, n, and n+1, the correlation value (SSD) of the coordinate n is the minimum. Thus, if the minimum point of the correlation value is selected without applying the parabola fitting, the coordinate n would be set as the minimum point.

On the other hand, when the parabola fitting in the spatial direction (coordinate direction) is applied near the coordinate n; for example, when the parabola fitting based on the correlation values (SSDs) of the coordinates n−1, n, and n+1 is used, it is possible to detect that there is a minimum point of the correlation value at a position slightly deviated from the coordinate n. For example, in the specific example of FIG. 16, based on a calculation formula based on correlation values In−1, In, In+1 respectively corresponding to the coordinates n−1, n, and n+1, a coordinate n' of the minimum point of the correlation value is calculated.

The trace processor 50 applies the parabola fitting in the spatial direction to, for example, the correlation value map, to derive the amount of change of each lattice point. For example, in the correlation value map of the time phase t shown in FIG. 15, with a two-dimensional parabola fitting using the correlation value corresponding to the coordinate (x+1, y) identified as the change destination of the lattice point (x, y) and the correlation value corresponding to the coordinate near this coordinate, the minimum point of the correlation value (coordinate corresponding to the minimum value) may be identified, and a change of the coordinate from the lattice point (x, y) to the minimum point may be set as the amount of change of the lattice point (x, y).

Without the use of the parabola fitting, the amount of change is in units of integers, obtained from the coordinate which is in units of integers, but with the use of the parabola fitting, an amount of change can be obtained in units of fractions smaller than the units of integers.

Referring back to FIG. 12, when the amount of change of the lattice point is derived, the amount of change of the measurement point is derived (S1207). The trace processor 50 derives the amount of movement of the measurement point based on, for example, amounts of change of a plurality of lattice points around the measurement point selected in S1202.

Figure 17:
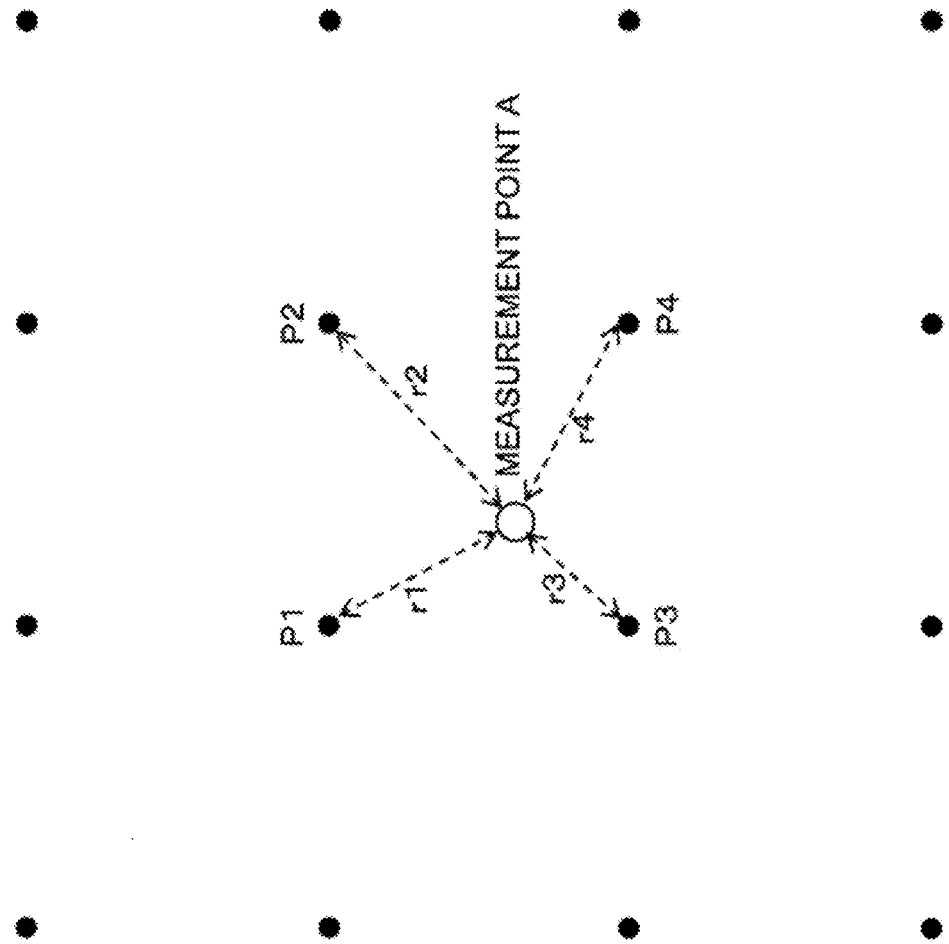
FIG. 17 is a diagram showing an example derivation of an amount of movement of a measurement point.

FIG. 17 is a diagram showing a derivation example of the amount of movement of the measurement point. FIG. 17 shows a specific example in which, when four lattice points P1~P4 surrounding a measurement point A are selected as a plurality of lattice points around the measurement point A, the amount of movement of the measurement point A is derived from amounts of change of the four lattice points P1~P4.

For example, amounts of change (vector quantities) of the four lattice points P1~P4 are added with weights according to distances r1~r4 from the lattice points P1~P4 to the measurement point A, to calculate the amount of movement (vector quantity) of the measurement point A.

Referring back to FIG. 12, the processes from S1201 to S1207 are executed for all frame data included in the frame data of the plurality of time phases acquired in S801 (FIG. 8), and when it is confirmed that the process targeted to all frame data is completed (S1208), the path optimization process exemplified in FIG. 12 is completed. With this process, for the frame data of the plurality of time phases acquired in S801 (FIG. 8), the amount of movement of the measurement point is derived for each time phase, and the movement destination of the measurement point is traced over the plurality of time phases.

Alternatively, in the second tracing process, there may be executed a tracing process to progress the process in the reverse direction of the time axis from the tracing process to progress the process in the forward direction of the time axis.

In the process of the forward direction, the trace processor 50 generates, for example, the correlation value map exemplified in FIG. 11 in the order of the time phase t, the time phase t+1, and the time phase t+2, executes the forward trace exemplified in FIG. 13 in the order of the time phase t, the time phase t+1, and the time phase t+2, and executes the back trace exemplified in FIG. 15 in the order of the time phase t+2, the time phase t+2, and the time phase t. The trace processor 50 then derives the amounts of movement of the measurement points in the order of the time phase t, the time phase t+1, and the time phase t+2, and traces the movement destinations of the measurement points.

On the other hand, in the process in the reverse direction, the trace processor 50 generates, for example, the correlation value map exemplified in FIG. 11 in the order of the time phase t+2, the time phase t+1, and the time phase t, executes the forward trace exemplified in FIG. 13 in the order of the time phase t+2, the time phase t+1, and the time phase t, and executes the back trace exemplified in FIG. 15 in the order of the time phase t, the time phase t+1, and the time phase t+2. Then, the trace processor 50 derives the amounts of movement of the measurement points in the order of the time phase t+2, the time phase t+1, and the time phase t, and traces the movement destinations of the measurement points.

With this process, between two adjacent diastoles (end-diastoles ED), a trace result of each measurement point from one diastole to the other diastole is obtained as a processing result in the forward direction, and a trace result of each measurement point from the other diastole to the one diastole is obtained as a processing result in the reverse direction.

The trace processor 50 may then combine the trace result obtained by the process in the forward direction of the time axis and the trace result obtained by the process in the reverse direction of the time axis, to obtain a final trace result.

When the trace result of the forward direction and the trace result of the reverse direction are to be combined, a process described in JP 5918325 B (refer to FIG. 6 or the like of JP 5918325 B) may be utilized. For example, the trace result in the forward direction from one diastole as a starting point to the other diastole, and the trace result in the reverse direction from the other diastole as the starting point to the one diastole may be added with weights according to a ratio corresponding to a temporal distance from the time phase which is the starting point, to obtain the combined trace result.

For example, the movement destination of each measurement point is traced by the specific example described above. For example, in the FS measurement, movement destinations of two measurement points which are set for the heart of the fetus are traced, and an analysis result such as the FS measurement value obtained based on the trace result or a waveform showing a distance between the two measurement points which changes over a plurality of time phases is displayed on the display 72 (refer to (6) in FIG. 2).

In addition, with the specific example of the tracing process described above, for example, an amount of spatial movement of one or more sites of interest may be derived over a plurality of time phases, and a vector display image showing a size and a direction of the amount of movement may be generated.

Figure 18:
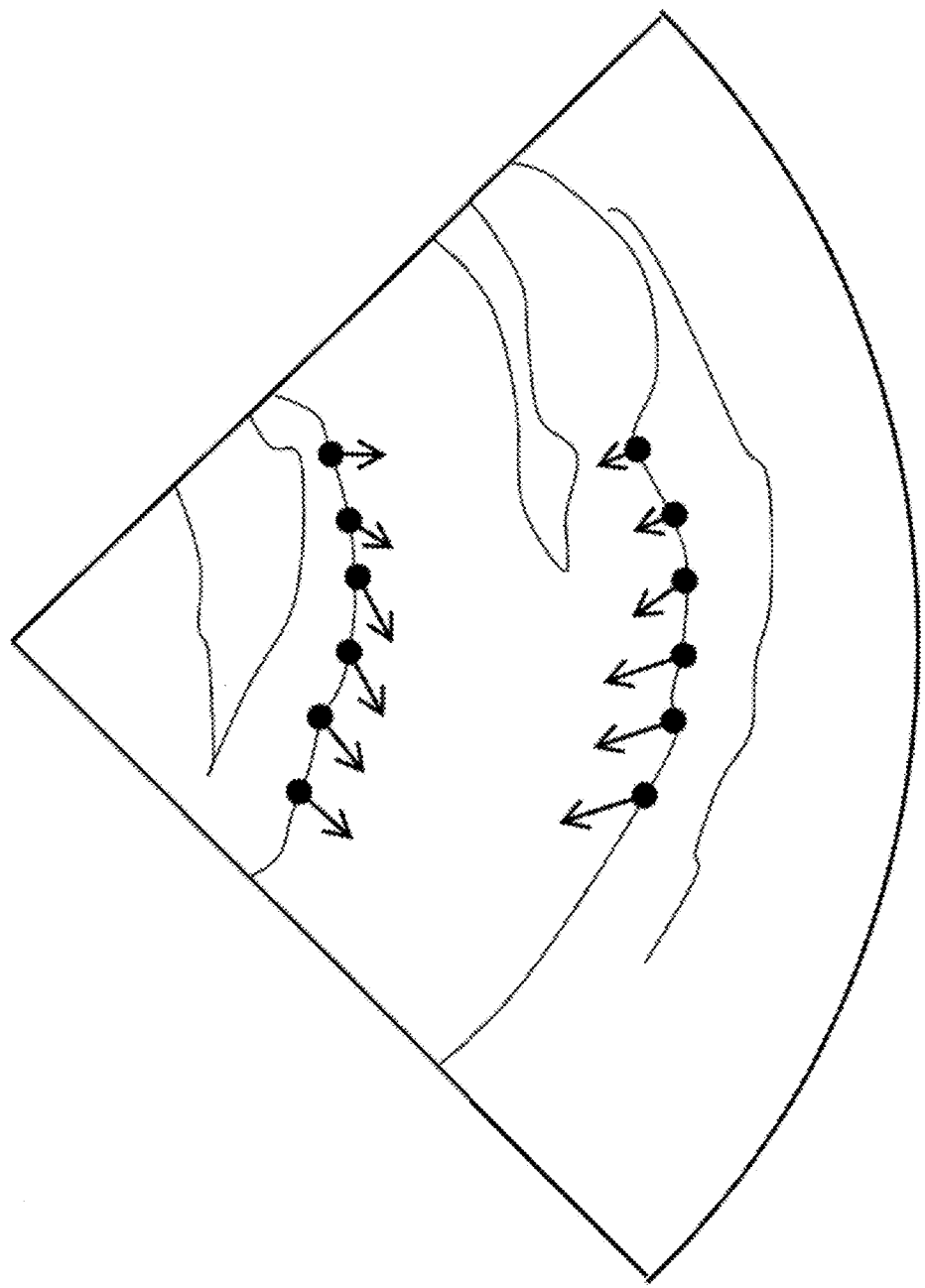
FIG. 18 is a diagram showing a specific example of a vector display image.

FIG. 18 is a diagram showing a specific example of the vector display image. FIG. 18 shows a specific example of the vector display image formed by the display image former 70 and displayed on the display 72. FIG. 18 exemplifies a vector display image in which the amount of movement (vector quantity) corresponding to each of a plurality of sites of interest is shown by an arrow. For example, the size of the amount of movement is expressed by a length or a size of the arrow, and a direction of the arrow is correlated to a direction of the amount of movement. Alternatively, the size and the direction of the amount of movement may be shown by a display form other than the arrow.

Alternatively, the trace processor 50 may derive an amount of movement for a plurality of sites of interest related to a diagnosis target involving a motion (including at least one of transfer or movement) of a heart (including a heart of an adult), a blood vessel, or the like, the display image former 70 may form a vector display image showing the amount of movement of the plurality of sites of interest related to the diagnosis target, and the display 72 may display the vector display image.

An embodiment of the present disclosure has been described. The above-described embodiment, however, is merely exemplary from all viewpoints, and does not limit the scope of the present disclosure. The present disclosure includes various modifications within the scope and spirit of the disclosure.

The invention claimed is:

1. An ultrasound diagnostic apparatus, configured to:
set frame data of a plurality of time phases, obtained by transmitting and receiving ultrasound to and from a diagnosis target of the ultrasound diagnostic apparatus, as a processing target;
derive an amount of temporal change at each coordinate of interest of a plurality of coordinates of interest which are spatially fixed in the frame data over the plurality of time phases;
set one or more sites of interest in the diagnosis target in frame data of a particular time phase of the plurality of time phases; and
derive an amount of spatial movement of each of the one or more sites of interest based on the amount of temporal change at one or more of the plurality of coordinates of interest.

2. The ultrasound diagnostic apparatus according to claim 1, wherein
a distribution of correlation values is generated for each coordinate of interest by a correlation calculation between time phases based on frame data in a target period which is a processing target among the plurality of time phases, and
the amount of temporal change at each coordinate of interest is derived based on the distribution of the correlation values obtained for each coordinate of interest.

3. The ultrasound diagnostic apparatus according to claim 2, wherein
dynamic programming in a time axis direction is applied to the distribution of the correlation values obtained for each time phase over a plurality of time phases in the target period for each coordinate of interest, to derive the amount of temporal change at each coordinate of interest.

4. The ultrasound diagnostic apparatus according to claim 1, comprising:
a detector that detects a plurality of key frames corresponding to a distinct time phase from among the frame data of the plurality of time phases collected by transmitting and receiving the ultrasound; and
a processor that sequentially sets, as a processing target, frame data of a plurality of time phases from a time phase corresponding to one of two key frames included in the plurality of key frames to a time phase corresponding to the other of the two key frames, and that derives the amount of temporal change of a tissue at a fixed position corresponding to each coordinate of interest.

5. The ultrasound diagnostic apparatus according to claim 4, wherein
the processor derives the amount of spatial movement of each site of interest for each time phase over a plurality of time phases in a trace period which is a target of tracing, and traces a motion of each site of interest over the plurality of time phases in the trace period based on an amount of movement derived for each time phase.

6. The ultrasound diagnostic apparatus according claim 4, wherein
the processor generates a correlation value map showing a distribution of correlation values for each coordinate of interest by a correlation calculation between time phases based on the frame data in a target period which is a processing target, and applies dynamic programming in a time axis direction to the correlation value map obtained for each time phase over a plurality of time phases in the target period for each coordinate of interest, to derive the amount of temporal change at each coordinate of interest.

7. The ultrasound diagnostic apparatus according to claim 5, wherein
the processor generates a correlation value map showing a distribution of correlation values for each coordinate of interest by a correlation calculation between time phases based on the frame data in a target period which is a processing target, and applies dynamic programming in a time axis direction to the correlation value map obtained for each time phase over a plurality of time phases in the target period for each coordinate of interest, to derive the amount of temporal change at each coordinate of interest.

8. The ultrasound diagnostic apparatus according to claim 6, wherein
the processor applies parabola fitting in a spatial direction to the correlation value map obtained for each coordinate of interest, to derive the amount of temporal change at each coordinate of interest.

9. The ultrasound diagnostic apparatus according to claim 5, wherein
a vector display image showing a size and a direction of the amount of spatial movement of each site of interest is generated and displayed.

10. A non-transitory computer-readable medium storing a program which, when executed, causes a computer to realize functions to:
set frame data of a plurality of time phases, obtained by transmitting and receiving an ultrasound to and from a diagnosis target of the ultrasound diagnostic apparatus, as a processing target;
derive an amount of temporal change at each coordinate of interest of a plurality of coordinates of interest which are spatially fixed in the frame data over the plurality of time phases;
set one or more sites of interest in the diagnosis target in frame data of a particular time phase of the plurality of time phases; and
derive an amount of spatial movement of each of the one or more sites of interest based on the amount of temporal change at one or more of the plurality of coordinates of interest.

\* \* \* \* \*